United States Patent [19]

Birbaum et al.

[11] Patent Number: 5,959,008
[45] Date of Patent: Sep. 28, 1999

[54] HYDROXYPHENYLTRIAZINES

[75] Inventors: Jean-Luc Birbaum, Kobe, Japan; Vien Van Toan, Lentigny, Switzerland; Andreas Valet, Binzen, Germany; Roger Meuwly, Cournillens, Switzerland

[73] Assignee: Ciba Specialty Chemicals Corp., Tarrytown, N.Y.

[21] Appl. No.: 08/828,200

[22] Filed: Mar. 21, 1997

[30] Foreign Application Priority Data

Mar. 26, 1996 [CH] Switzerland ............................. 0783/96

[51] Int. Cl.$^6$ ........................ C08K 5/3492; C07D 251/24
[52] U.S. Cl. ............................ 524/100; 524/91; 252/403; 544/216
[58] Field of Search ................... 524/91, 100; 252/403; 544/215, 216

[56] References Cited

U.S. PATENT DOCUMENTS

| 4,812,500 | 3/1989 | Hayden | 524/99 |
| 5,057,397 | 10/1991 | Miyabe et al. | 430/270 |
| 5,322,868 | 6/1994 | Valet et al. | 524/89 |
| 5,665,885 | 9/1997 | Steinmann | 546/242 |

FOREIGN PATENT DOCUMENTS

| 0434608 | 6/1991 | European Pat. Off. . |
| 0442847 | 8/1991 | European Pat. Off. . |
| 0502816 | 9/1992 | European Pat. Off. . |
| 0519298 | 12/1992 | European Pat. Off. . |
| 2278115 | 11/1994 | United Kingdom . |
| 2293823 | 4/1996 | United Kingdom . |

OTHER PUBLICATIONS

Derwent Abstr. 92–302100/199237 for EP 502816.

Derwent Abstr. 92–425542/199252 for EP 519298.

Derwent Abstr. 88–343153/198848.

*Primary Examiner*—Kriellion S. Morgan
*Attorney, Agent, or Firm*—Luther A. R. Hall

[57] ABSTRACT

Compositions based on synthetic organic polymers or pre-polymers are effectively stabilized against the damaging effects of light, oxygen and/or heat by addition of a compound of the formula I

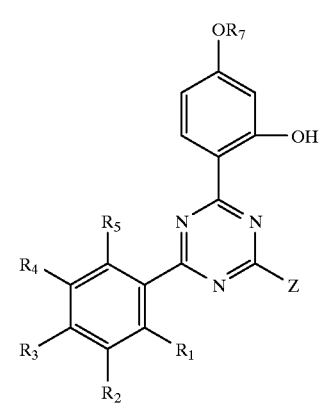
(I)

in which Z is a group of one of the formulae II or III,

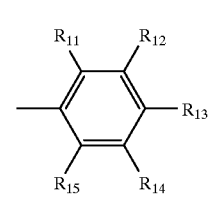
(II)

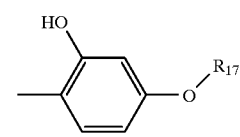

(III)

$R_7$ and $R_{17}$, independently of one another, are a radical of one of the formulae IV, V and VI

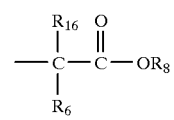
(IV)

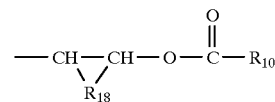

(V)

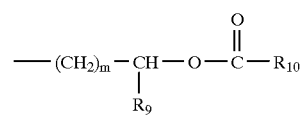

(VI)

and the remaining symbols are as defined in claim 1.

17 Claims, No Drawings

HYDROXYPHENYLTRIAZINES

The invention relates to synthetic organic polymers or prepolymers, especially coating material which is stabilized by adding one or more 2-(2'-hydroxyphenyl)-4,6-diaryl-1,3,5-triazines, to novel compounds of this type, and to the use of these compounds as stabilizers.

If it is desired to increase the photostability of an organic material, for example a coating, it is common to add a light stabilizer. One very frequently employed class of light stabilizers are the UV absorbers, which protect the material by absorbing the harmful radiation via chromophores. One important group of UV absorbers is the triphenyl-triazines; compounds of this type comprising acid groups or ester groups are described, inter alia, in the publications U.S. Pat. No. 3,244,708, U.S. Pat. No. 3,249,608, CH-A-484695, GB-A-1,321,561 and U.S. Pat. No. 4,826,978.

The documents EP-A-434,608, EP-A-530,135, U.S. Pat. No. 5,364,749 and GB-A-2,273,498 also mention individual compounds of this class having branched ester side chains.

For a compound to be efficient as a stabilizer, properties of critical importance are not only its spectral and antioxidant properties but also, inter alia, its compatibility with the material to be stabilized, and its solubility.

It has now been found that certain compounds of the 2-(2'-hydroxyphenyl)-4,6-diaryl-1,3,5-triazine type, comprising specific branched acid or ester side chains, surprisingly possess particularly good stabilizer properties for synthetic organic polymers and prepolymers.

The invention therefore initially provides a composition comprising
A) a synthetic organic polymer or prepolymer and
B) as stabilizer against the damaging effect of light, oxygen and/or heat, a compound of the formula I

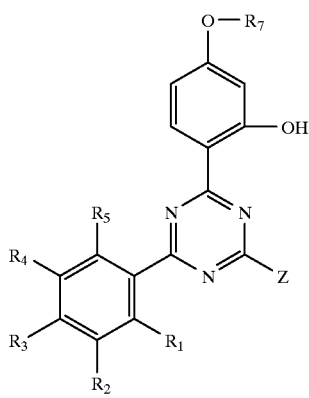

(I)

in which Z is a group of the formula II

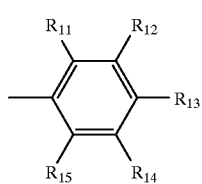

(II)

or a group of the formula III

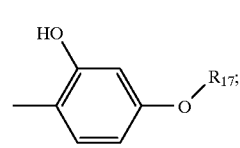

(III)

$R_1$, $R_5$, $R_{11}$, and $R_{15}$, independently of one another, are H, $C_1$–$C_{12}$alkyl, $C_3$–$C_6$alkenyl, $C_1$–$C_{12}$alkoxy, $C_3$–$C_6$alkenoxy, halogen or —CN;

$R_2$, $R_3$, $R_4$, $R_{12}$, $R_{13}$ and $R_{14}$, independently of one another, are H, $C_1$–$C_{12}$alkyl, $C_2$–$C_6$alkenyl, $C_1$–$C_{12}$alkoxy, $C_3$–$C_6$alkenoxy, phenyl, halogen, trifluoromethyl; $C_7$–$C_{11}$ phenylalkyl; phenyloxy; or —CN;

$R_7$ and $R_{17}$, independently of one another, are a radical of one of the formulae IV, V and VI

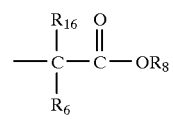

(IV)

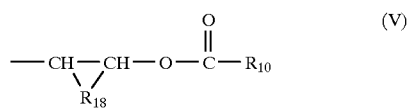

(V)

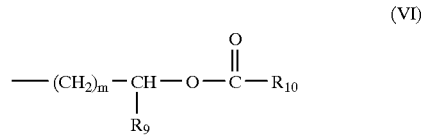

(VI)

in which m is a number from the range 1 to 12;
$R_6$ is $C_1$–$C_{16}$alkyl, —COOR$_8$ or phenyl;
$R_8$ is H, $C_1$–$C_{18}$alkyl, $C_3$–$C_{18}$alkenyl, $C_5$–$C_{12}$cycloalkyl, $C_1$–$C_4$alkylcyclohexyl, phenyl, $C_7$–$C_{14}$alkylphenyl, $C_6$–$C_{15}$bicycloalkyl, $C_6$–$C_{15}$-bicycloalkenyl, $C_6$–$C_{15}$tricycloalkyl, $C_6$–$C_{15}$bicycloalkyl-alkyl or $C_7$–$C_{11}$phenylalkyl, and, if Z is a group of the formula II, additionally comprises $C_2$–$C_{50}$alkyl interrupted by O;
$R_9$ is $C_2$–$C_{14}$alkyl, phenyl, or $C_2$–$C_{50}$alkyl interrupted by O; or is $C_1$–$C_{14}$alkyl which is substituted by phenyl, phenoxy, $C_1$–$C_4$alkylcyclohexyl, $C_1$–$C_4$alkylcyclohexyloxy, $C_5$–$C_{12}$cycloalkyl or $C_5$–$C_{12}$cycloalkoxy;
$R_{10}$ is H, $C_1$–$C_{17}$alkyl, $C_1$–$C_{12}$alkoxy, phenoxy, phenyl, $C_7$–$C_{11}$phenylalkyl, $C_7$–$C_{14}$alkylphenoxy, $C_7$–$C_{11}$phenylalkoxy, $C_6$–$C_{12}$cycloalkyl, $C_1$–$C_4$alkylcyclohexyloxy, $C_6$–$C_{12}$cycloalkoxy, $C_7$–$C_{11}$cyclohexylalkyl, $C_7$–$C_{11}$cyclohexylalkoxy, $C_6$–$C_{15}$bicycloalkyl, $C_6$–$C_{15}$bicycloalkenyl, $C_6$–$C_{15}$tricycloalkyl, $C_6$–$C_{15}$bicycloalkoxy, $C_6$–$C_{15}$bicycloalkenoxy, $C_6$–$C_{15}$tricycloalkoxy or phenyl-NH—;
$R_{16}$ is hydrogen or is as defined for $R_6$; or $R_6$ and $R_{16}$ together are $C_4$–$C_{11}$alkylene; and
$R_{18}$ is $C_3$–$C_{10}$alkylene,
with the exception of those compounds in which Z is a group of the formula III and $R_1$ and $R_5$ are both alkyl, and of those in which $R_3$ or $R_{13}$ is phenyl and $R_7$ or $R_{17}$ is a radical of the formula VI or $R_{16}$ is hydrogen.

Of particular industrial importance are compositions in which, in the compound of component B,
$R_1$, $R_5$, $R_{11}$ and $R_{15}$, independently of one another, are H, $C_1$–$C_{12}$alkyl, $C_3$–$C_6$alkenyl, $C_1$–$C_{12}$alkoxy, $C_3$–$C_6$alkenoxy, halogen or —CN;

$R_2$, $R_3$, $R_4$, $R_{12}$, $R_{13}$ and $R_{14}$, independently of one another, are H, $C_1$–$C_{12}$alkyl, $C_2$–$C_6$alkenyl, $C_1$–$C_{12}$alkoxy, $C_3$–$C_6$alkenoxy, phenyl, halogen, trifluoromethyl;

$C_7$–$C_{11}$phenylalkyl; phenyloxy; or —CN;

$R_7$ and $R_{17}$, independently of one another, are a radical of one of the formulae IV, V and VI

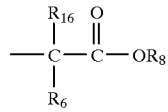
(IV)

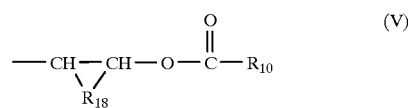
(V)

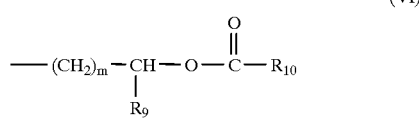
(VI)

in which m is a number from the range 1 to 12;

$R_6$ is $C_1$–$C_{16}$alkyl, —COOR$_8$ or phenyl;

$R_8$ is H, $C_1$–$C_{18}$alkyl, $C_3$–$C_{18}$alkenyl, $C_5$–$C_{12}$cycloalkyl, $C_1$–$C_4$alkylcyclohexyl, phenyl, $C_7$–$C_{14}$alkylphenyl or $C_7$–$C_{11}$phenylalkyl and, if Z is a group of the formula II, additionally comprises $C_2$–$C_{18}$alkyl interrupted by O;

$R_9$ is $C_2$–$C_{14}$alkyl, phenyl or $C_2$–$C_{14}$alkyl interrupted by O; or is $C_1$–$C_{14}$alkyl which is substituted by phenyl, phenoxy, $C_1$–$C_4$alkylcyclohexyl, $C_1$–$C_4$alkylcyclohexyloxy, $C_5$–$C_{12}$cycloalkyl or $C_5$–$C_{12}$cycloalkoxy;

$R_{10}$ is H, $C_1$–$C_{17}$alkyl, $C_1$–$C_{12}$alkoxy, phenoxy, phenyl, $C_7$–$C_{11}$phenylalkyl, $C_7$–$C_{14}$alkylphenoxy, $C_7$–$C_{11}$phenylalkoxy, $C_6$–$C_{12}$cycloalkyl, $C_1$–$C_4$alkylcyclohexyloxy, $C_6$–$C_{12}$cycloalkoxy, $C_7$–$C_{11}$cyclohexylalkyl, $C_7$–$C_{11}$cyclohexylalkoxy or phenyl-NH—;

$R_{16}$ is hydrogen or is as defined for $R_6$; and $R_{18}$ is $C_3$–$C_{10}$alkylene, with the exception of those compounds in which Z is a group of the formula III and $R_1$ and $R_5$ are both alkyl, and of those in which $R_3$ or $R_{13}$ is phenyl and $R_7$ or $R_{17}$ is a radical of the formula VI or $R_{16}$ is hydrogen.

Component (A) above does not include photosensitive materials comprising silver halide emulsion layers.

The prepolymers referred to above are to be understood as meaning those monomeric or oligomeric compounds which, under the influence of heat or radiation, for example UV radiation, electron beams or X-rays, and/or under the influence of chemical components such as crosslinkers, couplers or catalysts, can be converted into the high molecular mass form (polymer).

The invention also provides for the use of compounds of the formula I as stabilizers for synthetic organic polymers or prepolymers against damage by light, oxygen or heat. The compounds of the formula I are especially suitable as light stabilizers (UV absorbers). Of particular interest is their use in synthetic organic polymers or prepolymers, as are present in plastics, rubbers, adhesives or, in particular, in coating materials. Examples of polymers which can be stabilized in this way are the following:

1. Polymers of monoolefins and diolefins, for example polypropylene polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic denvatives, for example styrene/butadiene, styrene/acrylonitrile, styrene/alkyl methaciylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention also provides a process for stabilizing synthetic organic polymers or prepolymers against damage by light, oxygen and/or heat, which comprises adding thereto a compound of the formula I as stabilizer.

The amount of stabilizer to be used depends on the organic material to be stabilized and on the intended use of the stabilized material. In general the novel composition comprises from 0.01 to 15 parts by weight, in particular from 0.05 to 10 parts by weight and, especially, from 0.1 to 5 parts by weight of the stabilizer (component B) per 100 parts by weight of component A.

In addition to the stabilizer of the formula I the novel compositions may include other stabilizers or other additives, examples being antioxidants, further light stabilizers, metal deactivators, phosphites or phosphonites. Examples thereof are the following stabilizers:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclo-hexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methyl-undec-1'-yl)phenol, 2,4-dimethyl-6-(1'-methylheptadec-1'-yl)phenol, 2,4-dimethyl-6-(1'- methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxy-anisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thio-bis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(a-methyl-cyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1, 1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmer-captobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O—, N— and S-benzyl compounds, for example 3,5,3', 5'-tetra-tert-butyl-4,4'-dihydroxy-dibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)-amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyi-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxy-anilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-di-methylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosnhonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzyl-phosphonate, the calcium salt of the monoethyl ester of 3,5-di-tert-butyl-4-hydroxybenzyl-phosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)-diphenylamine, N,N'-dimethyl-N,N'-di-sec-butyl-p-phenylenediamine, diphenylamine, N-allyldiphenylamine, 4-isopropoxydiphenylaamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, Bis[4-(1',3'-dimethylbutyl) phenyl]amine, tert-octylated N-phenyl-1-naphthylamine, a mixture of mono- and dialkylated tert-butyl/tert-octyldiphenyl- amines, a mixture of mono- and dialkylated nonyldiphenylamines, a mixture of mono- and dialkylated dodecyldiphenylamines, a mixture of mono- and dialkylated isopropyl/isohex-yldiphenylamines, a mixture of mono- und dialkylated tert-butyldiphenylamines, 2,3-di-hydro-3,3-dimethyl-4 H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpipe-rid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)- benzotriazole, 2-(3',5'-di-tert-butyl-2'-hydroxyphenyl)benzotriazole, 2-(5'-tert-butyl-2'- hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycar-bonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-( 3'-tert-butyl-2'-hydroxy-5'-(2-octyl-oxycarbonylethyl) phenyl)benzotriazole, 2-(3'-tert-butyl-5'-[2-(2-ethylhexyloxy)carbonyl-ethyl]-2'-hydroxyphenyl) benzotriazole, 2-(3'-dodecyl-2'-hydroxy-5'-methylphenyl) benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2 H-benzotriazole with polyethylene glycol 300; [R—CH$_2$CH$_2$—COO(CH$_2$)$_3$—]$_2$, where R=3'-tert-butyl-4'-hydroxy-5'-2 H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxy-benzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-p-cyanovinyl)-2-methylindoline.

2.5. Nickel compounds, for example nickel complexes of 2,2'-thio-bis-[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldi-thiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate,
bis(2,2,6,6-tetramethyl-4-piperidyl)succinate,
bis(1,2,2,6,6-pentamethyl-4-piperidyl)sebacate,
bis(1-octyloxy-2,2,6,6-tetramethyl-4-piperidyl)sebacate,
bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butyl-benzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, po the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6- trichloro-1,3,5-triazine as well as 4-butylamino-2,2,6,6-tetramethylpiperidine (CAS Reg. No. [136504-96-6]);

N-(2,2,6,6-tetramethyl-4-piperidyl)-n-dodecylsuccinimid,

N-(1,2,2,6,6-pentamethyl-4-piperidyl)-n-dodecylsuccinimid, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro [4,5]decane and epichlorohydrin, propanedioic acid (4-methoxyphenyl)-methylene-bis(1,2,2,6,6-pentamethyl-4-piperidyl) ester, N,N'-bis-formyl-N,N'-bis(2,2,6,6-tetramethyl-4-piperidyl)-hexamethylenediamine, poly-[methylpropyl-3-oxy-4-(2,2,6,6-tetramethyl-4-piperidyl)]-siloxane, a reaction product of maleic acid-α-olefin copolymer and 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy- 4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis (2,4dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenyl-propionyl) hydrazine, 3-salicyloylamino-1,2,4-triazole, bis(benzylidene)oxalyl di-hydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)-thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyl-oxypentaerythritol diphosphite, bis(2,4-di-tert-butyl-6-methylphenyl)pentaerythritol diphosphite, bis(2,4,6-tris (tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12 H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhy-droxylamine, N,N-dihexadecylhydroxylamine, N,N-dioctadecylhydroxylamine, N-hexa-decyl-N-octadecylhydroxylamine, N-heptadecyl-N-octadecylhydroxylamine, N,N-dialkyl-hydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecylalpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4,316,611, DE-A-4,316,622, DE-A-4,316,876, EP-A-0,589,839 or EP-A-0,591,102 or 3-[4-(2-acetoxyethoxy)phenyl]-5,7-di-tert-butyl-benzofuran-2-one, 5,7-di-tert-butyl-3-[4-(2-stearoyl-oxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4piva-loyloxyphenyl)-5,7-di-tert-butyl-benzofuran-2-one.

The nature and amount of the further stabilizers added is determined by the nature of the substrate that is to be stabilized and by its intended use; in many cases, from 0.1 to 5% by weight is used, based on the polymer to be stabilized.

The compounds of the formula I can be employed with particular advantage in compositions comprising as component A a thermoplastic polymer or a binder for coatings, for example paints.

Examples of suitable thermoplastic polymers are polyolefins, polymers comprising heteroatoms in the main chain, for example thermoplastic polymers whose main chain comprises nitrogen, oxygen and/or sulfur, especially nitrogen or oxygen.

Incorporation into the synthetic organic polymers or prepolymers can be effected by adding the novel compounds and, if desired, further additives by the methods customary in the art. Incorporation can expediently take place prior to or in the course of shaping, for example by mixing the pulverulent components or by adding the stabilizer to the melt or solution of the polymer, or by applying the dissolved or dispersed compounds to the polymer, with or without subsequent evaporation of the solvent. Where elastomers are involved they can also be stabilized as latices. Another possible way of incorporating the novel compounds into polymers is to add them before or during polymerization of the corresponding monomers and/or prior to crosslinking.

The novel compounds or mixtures thereof can also be added to the plastics that are to be stabilized in the form of a masterbatch, containing these compounds in, for example, a concentration of from 2.5 to 25% by weight.

The novel compounds can expediently be incorporated by the following methods;

as an emulsion or dispersion (for example to latices or emulsion polymers)

as a dry mix during the mixing of additional components or polymer mixtures by direct addition to the processing equipment (e.g. extruders, internal mixers, etc.)

as a solution or melt.

The stabilized polymer compositions obtained in this way can be converted into shaped articles, for example fibres, films, tapes, sheets, multi-wall sheets, containers, tubes and other profiles, by conventional methods, for example by hot pressing, spinning, extrusion or injection moulding.

The invention therefore additionally provides for the use of the novel polymer composition for producing a shaped article.

Use in multilayer systems is also of interest. In this case, a novel polymer composition having a relatively high content of stabilizer of the formula I, for example 1–15% by weight, is applied in a thin film (10–100 μm) to a shaped article made from a polymer containing little or no stabilizer of the formula I. Application can be carried out at the same time as shaping of the article, for example by coextrusion. However, application can also be made to the ready-shaped article, for example by lamination with a film or by coating with a solution. The outer layer or layers of the finished article have the function of a UV filter which protects the interior of the article against UV light. The outer layer preferably contains 1–15% by weight, in particular 5–10% by weight, of at least one stabilizer of the formula I.

The use of the novel polymer composition for producing multilayer systems in which the outer layer(s) in a thickness of 10–100 μm consists of a novel polymer composition while the inner layer contains little or no stabilizer of the formula I is therefore also provided by the invention.

The polymers stabilized in this way are notable for high weathering resistance, and especially for high resistance to UV light. They thus retain their mechanical properties and their colour and gloss even when used outdoors for a long period.

The use of the novel compounds of the formula I as stabilizers for coatings, especially for paints, is of particular interest. The invention therefore also provides those compositions in which component A is a film-forming binder.

The novel coating composition preferably contains 0.01–10 parts by weight of B, in particular 0.05–10 parts by weight of B, especially 0.1–5 parts by weight of B, per 100 parts by weight of solid binder A.

Here again, multicoat systems are possible, where the concentration of the compound of the formula I (component B) in the topcoat can be higher, for example from 1 to 15 parts by weight of B, especially 3–10 parts by weight of B per 100 parts by weight of solid binder A.

The use of the compound of the formula I as stabilizer in coatings brings with it the additional advantage that the delamination, i.e. the flaking of the coating from the substrate, is prevented. This advantage is particularly marked in the case of metallic substrates, and also in the case of multicoat systems on metallic substrates.

Suitable binders (component A) are in principle all those which are customary in the art for example those as described in Ullmann's Encyclopedia of Industrial Chemistry, 5th Ed., Vol. A18, pp.368–426, VCH, Weinheip 1991. The substance involved is generally a film-forming binder based on a thermoplastic or thermosetting resin, predominantly on a thermosetting resin. Examples thereof are alkyd, acrylic, polyester, phienolic, melamine, epoxy and polyurethane resins and mixtures thereof.

Component A can be a cold-curable or a hot-curable binder, the addition of a curing catalyst possibly being of advantage. Examples of suitable catalysts which accelerate the curing of the binder are described in Ullmann's Encyclopedia of Industrial Chemistry, Vol. A 18, p. 469, VCH Verlagsgesellschaft, Weinheim 1991.

Preference is given to coating compositions in which component A is a binder comprising a functional acrylate resin and a crosslinker.

Examples of co ating compositions with specific binders are:

1. paints based on cold- or hot-crosslinkable alkyd, acrylate, polyester, epoxy or melamine resins or mixtures of such resins, with or without addition of a curing catalyst;
2. two-component polyurethane paints based on hydroxyl-containing acrylate, polyester or polyether resins and on aliphatic or aromatic isocyanates, isocyanurates or polyisocyanates;
3. one-component polyurethane paints based on block isocyanates, isocyanurates or polyisocyanates which are deblocked in the course of stoving;
4. two-component paints based on (poly)ketimines and on aliphatic or aromatic isocyanates, isocyanurates or polyisocyanates;
5. two-component paints based on (poly)ketimines and an unsaturated acrylate resin or a polyacetoacetate resin or a methacrylamidoglycolate methyl ester;
6. two-component paints based on carboxyl- or amino-containing polyacrylates and polyepoxides;
7. two-component paints based on acrylate resins containing anhydride groups and on a polyhydroxy or polyamino component;
8. two-component paints based on acrylate-containing anhydrides and polyepoxides;
9. two-component paints based on (poly)oxazolines and on acrylate resins containing anhydride groups, or unsaturated acrylate resins or aliphatic or aromatic isocyanates, isocyanurates or polyisocyanates;
10. two-component paints based on unsaturated polyacrylates and polymalonates;
11. thermoplastic polyacrylate paints based on thermoplastic acrylate resins or externally crosslinking acrylate resins in combination withetherified melamine resins;
12. paint systems based on siloxane-modified or fluorine-modified acrylate resins.

The novel coating compositions can also be radiation-curable. In this case the binder essentially comprises monomeric or oligomeric compounds containing ethylenically unsaturated bonds (prepolymers) which are cured, after application, by UV radiation or electron beams, i.e. are converted into a crosslinked, high molecular mass form. Corresponding systems are described in the above-mentioned publication, Ullmann's Encylopedia of Industrial Chemistry, 5th Ed., Vol. A18, pages 451–453. In radiation-curable coating compositions the compounds of the formula I may be employed even without the addition of sterically hindered amines.

In addition to components A and B, the novel coating composition preferably comprises, as component C, a light stabilizer of the sterically hindered amine, 2-(2-hydroxyphenyl)-1,3,5-triazine and/or 2-hydroxyphenyl-2 H-benzotriazole type, for example as mentioned in the above list under items 2.1, 2.6 and 2.8. Of particular industrial interest in this context is the addition of 2-mono-resorcinyl-4,6-diaryl-1,3,5-triazines and/or 2-hydroxyphenyl-2 H-benzotriazoles.

In order to achieve maximum light stability it is of particular interest to add sterically hindered amines as mentioned in the above list under 2.6. The invention therefore also provides a coating composition which, in addition to components A and B, comprises a light stabilizer of the sterically hindered amine type as component C.

This is preferably a 2,2,6,6-tetraalkylpiperidine derivative comprising at least one group of the formula

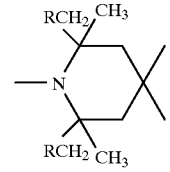

in which R is hydrogen or methyl, especially hydrogen.

Component C is preferably used in an amount of 0.05–5 parts by weight per 100 parts by weight of the solid binder.

Examples of tetraalkylpiperidine derivatives that can be used as component C are given in EP-A-356,677, pages 3–17, sections a) to f). Those sections of this EP-A are regarded as part of the present description. It is particularly expedient to employ the following tetraalkylpiperidine derivatives:

bis(2,2,6,6-tetramethylpiperidin-4-yl) succinate, bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) butyl-(3,5-di-tert-butyl-4-hydroxybenzyl)malonate, bis(1-octyloxy-2,2,6,6-tetramethylpiperidin-4-yl) sebacate, tetra(2,2,6,6-tetramethylpiperidin-4-yl)butane 1,2,3,4-tetracarboxylate, tetra(1,2,2,6,6-pentamethylpiperidin-4-yl)butane 1,2,3,4-tetracarboxylate, 2,2,4,4-tetramethyl-7-oxa-3,20-diaza-21-oxo-dispiro [5.1.11.2]heneicosane, 8-acetyl-3-dodecyl-1,3,8-triaza-7,7,9,9-tetramethylspiro [4.5]decane-2,4-dione, or a compound of the formulae

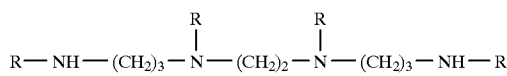

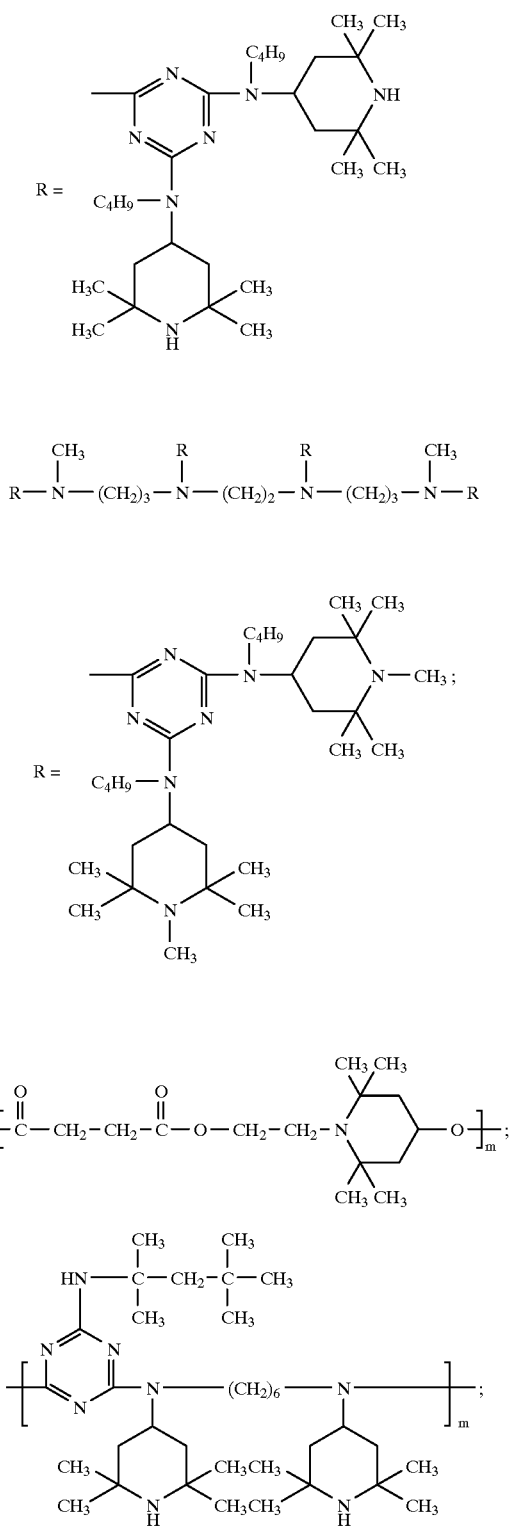

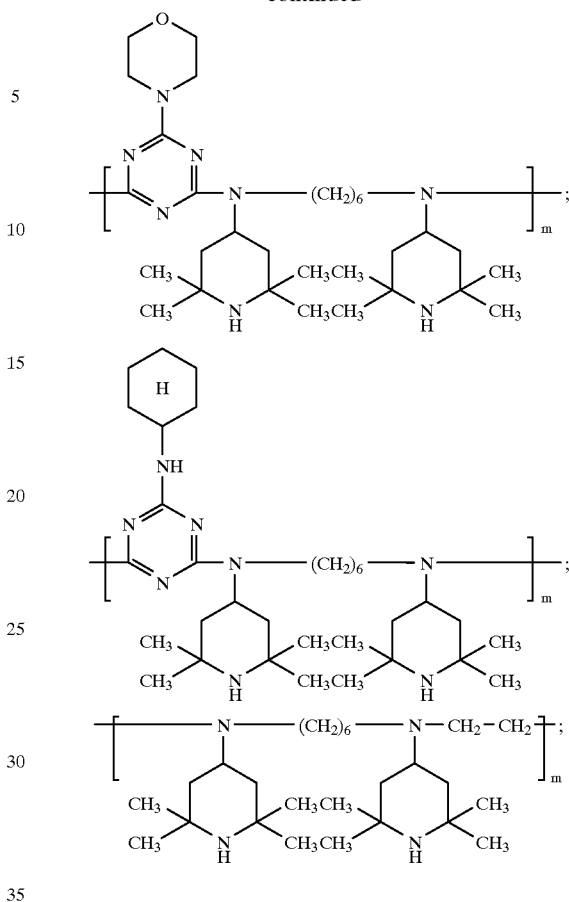

in which m is 5–50.

In addition to components A, B and, if used, C, the coating composition can comprise further components, examples being solvents, pigments, dyes, plasticizers, stabilizers, thixotropic agents, drying catalysts and/or levelling assistants. Examples of possible components are those as described in Ullmann's Encyclopedia of Industrial Chemistry, 5th Ed., Vol. A18, pp. 429–471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as, for example, organotin compounds.

Examples of metal carboxylates are the stearates of Pb, Mn or Zn, the octoates of Co, Zn or Cu, the naphthenates of Mn and Co, or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate and dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof.

Further examples are quaternary ammonium salts, for example trimethylbenzylammonium chloride.

Amino-containing resins are simultaneously binder and curing catalyst. Examples thereof are amino-containing acrylate copolymers.

The curing catalysts used can also be phosphines, for example triphenolphosphine.

The novel coating compositions may also be radiation-curable coating compositions. In this case the binder consists essentially of monomeric or oligomeric compounds having ethylenically unsaturated bonds, which following application are cured—i.e. converted to a crosslinked, high molecular mass form—by means of actinic radiation. Where the system involved is a UV curing system it generally comprises, in addition, a photoinitiator. Corresponding systems are described in the abovementioned publication, Ullmann's Encyclopedia of Industrial Chemistry, 5th Ed., Vol. A18, pages 451–453. In radiation-curable coating compositions the novel stabilizer mixtures can be employed even without the addition of sterically hindered amines.

The novel coating compositions can be applied to any desired substrates, for example to metal, wood, plastic or ceramic materials. They are preferably used as a topcoat in the painting of automobiles. Where the topcoat comprises two layers, of which the lower layer is pigmented and the upper layer is not pigmented, the novel coating composition can be used for the top or bottom layer or for both layers, but preferably for the upper layer.

The novel coating compositions can be applied to the substrates by the customary techniques, for example by spreading, spraying, curtain coating, dipping or electrophoresis; see also Ullmann's Encyclopedia of Industrial Chemistry, 5th Ed., Vol. A18, pp. 491–500.

Depending on the binder system, the coatings can be cured at room temperature or by heating. The coatings are preferably cured at 50–150° C., powder coatings also at higher temperatures.

The coatings obtained in accordance with the invention have excellent resistance to damaging effects of light, oxygen and heat; particular mention should be made of the good light stability and weathering resistance of the resulting coatings, for example paints.

The invention therefore also provides a coating, especially a paint, which has been stabilized against the damaging effects of light, oxygen and heat by adding a compound of the formula I. The paint is preferably a topcoat for automobiles. The invention additionally comprises a process for stabilizing a coating based on organic polymers against damage by light, oxygen and/or heat, which comprises admixing to the coating composition a compound of the formula I, and for the use of compounds of the formula I in coating compositions as stabilizers against damage by light, oxygen and/or heat.

The coating compositions can comprise an organic solvent or solvent mixture in which the binder is soluble. However, the coating composition can also be an aqueous solution or dispersion. The vehicle can also be a mixture of an organic solvent and water. The coating composition can be a high-solids paint or may be free from solvent (e.g. powder coating).

The pigments can be inorganic, organic or metallic pigments. The novel coating compositions preferably contain no pigments and are used as clearcoat.

Likewise preferred is the use of the coating composition as a topcoat for applications in the automobile industry, especially as pigmented or unpigmented topcoat of the paint system. However, use for underlying layers is also possible.

The stabilizer (component B) can also be a mixture of two or more compounds of the formula I.

Where two or more radicals of the same name occur within the same compound of the formula I, they can be identical or - within the scope of the possible definitions indicated—different.

A substituent halogen is —F, —Cl, —Br or —I; preference is given to —F, —Cl or —Br, especially to —Cl.

Alkylphenyl is alkyl-substituted phenyl; $C_7$–$C_{14}$alkylphenyl, for example, comprises methylphenyl (tolyl), dimethylphenyl (xylyl), trimethylphenyl (mesityl), ethylphenyl, propylphenyl, butylphenyl, dibutylphenyl, pentylphenyl, hexyiphenyl, heptylphenyl and ocltylphenyl.

Phenylalkyl is phenyl-substituted alkyl; $C_7$–$C_{11}$phenylalkyl, for example, comprises benzyl, α-methylbenzyl, α-ethylbenzyl, α,α-dimethylbenzyl, phenylethyl, phenylpropyl, phenylbutyl and phenylpentyl.

Glycidyl is 2,3-epoxypropyl.

n-alkyl or alkyl-n is an unbranched alkyl radical.

Alkyl interrupted by O may generally include one or more heteroatoms, in which case the oxygen atoms are not adjacent. Preferably, one carbon atom of the alkyl chain is bonded to not more than 1 oxygen atom.

Within the scope of the definitions indicated, alkyl radicals $R_1$, $R_2$, $R_3$, $R_4$, $R_5$, $R_6$, $R_8$, $R_9$, $R_{10}$, $R_{11}$, $R_{12}$, $R_{13}$, $R_{14}$, $R_{15}$ and $R_{16}$ are branched or unbranched alkyl such as methyl, ethyl, propyl, isopropyl, n-butyl, sec-butyl, isobutyl, t-butyl, 2-ethylburyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl. Preferably, $R_1$, $R_2$, $R_3$, $R_4$, $R_5$, $R_{11}$, $R_{12}$, $R_{13}$, $R_{14}$ and $R_{15}$ as alkyl are short-chain, e.g. $C_1$–$C_8$alkyl, especially $C_1$–$C_4$alkyl, such as methyl or butyl. $R_1$, $R_{11}$, $R_3$, $R_{13}$, $R_5$ and $R_{15}$ are, in particular, preferably methyl, ethyl or isopropyl.

$R_1$, $R_{11}$, $R_3$, $R_{13}$, $R_5$, $R_{15}$, $R_2$, $R_{12}$, $R_4$ and $R_{14}$ are preferably H, $C_1$–$C_{12}$alkyl, $C_1$–$C_{12}$alkoxy; especially H, $C_1$–$C_4$alkyl, $C_1$–$C_4$alkoxy; in particular H, methyl or methoxy. Of particular importance are compounds of the formula I in which $R_2$, $R_{12}$, $R_4$ and/or $R_{14}$ are phenyl.

$C_1$–$C_4$alkyl is, in particular, methyl, ethyl, isopropyl, n-butyl, 2-butyl, 2-methylpropyl or tertiary butyl.

Within the scope of the definitions indicated, alkenyl $R_1$, $R_{11}$, $R_3$, $R_{13}$, $R_5$, $R_{15}$, $R_2$, $R_{12}$, $R_4$, $R_{14}$ and $R_8$ embrace, inter alia, allyl, isopropenyl, 2-butenyl, 3-butenyl, isobutenyl, n-penta-2,4-dienyl, 3-methyl-but-2-enyl; $R_8$, additionally, comprises n-oct-2-enyl, n-dodec-2-enyl, isododecenyl, n-octadec-2-enyl, n-octadec-4-enyl. In the case of $R_2$, $R_{12}$, $R_3$, $R_{13}$, $R_4$ and $R_{14}$, the definition of vinyl is also possible, for example.

$R_9$ is preferably $C_2$–$C_{14}$alkyl, phenyl or —$CH_2$—O—$R_{19}$, especially $C_2$–$C_{14}$alkyl or —$CH_2$—O—$R_{19}$; $R_{19}$ here is phenyl, $C_7$–$C_{11}$phenylalkyl, $C_1$–$C_4$-alkylcyclohexyl, $C_5$–$C_{12}$cycloalkyl, $C_2$–$C_{13}$alkyl or $C_2$–$C_{13}$alkyl which is interrupted by —O—. Alkyl $R_9$ is particularly preferably $C_3$–$C_{13}$alkyl, especially $C_4$–$C_{13}$alkyl.

$R_{10}$ is preferably $C_1$–$C_{17}$alkyl, cyclohexyl or phenyl.

$R_{18}$ together with the carbon atoms attached to it forms a cycloalkyl ring; preference is given to cyclopentyl, cyclohexyl, cycloheptyl, cyclooctyl and cyclododecyl, especially cyclopentyl and cyclohexyl.

Preferred novel compositions are those in which, in the compound of the formula O, $R_1$, $R_5$, $R_{11}$ and $R_{15}$, independently of one another, are H, $C_1$–$C_4$alkyl, $C_3$alkenyl, $C_1$–$C_4$alkoxy, $C_3$–$C_6$alkenoxy, —F or —Cl;

$R_2$, $R_3$, $R_4$, $R_{12}$, $R_{13}$ and $R_{14}$, independently of one another, are H, $C_1$–$C_4$alkyl,
$C_3$–$C_6$alkenyl, $C_1$–$C_4$alkoxy, $C_3$–$C_6$alkenoxy, phenyl, —F, —Cl, or —CN;

$R_6$ is $C_1$–$C_{16}$alkyl or phenyl;

$R_8$ is H, $C_1$–$C_{18}$alkyl, $C_3$–$C_8$alkenyl, cyclohexyl, $C_1$–$C_4$alkylcyclohexyl, phenyl, norborn-2-yl, norborn-5-en-2-yl, norborn-2-methyl, norborn-5-ene-2-methyl or $C_7$–$C_{11}$phenylalkyl and, if Z is a group of the formula II, additionally comprises $C_2$–$C_{18}$alkyl interrupted by O;

$R_9$ is $C_2$–$C_{14}$alkyl or $C_3$–$C_{14}$alkyl interrupted by O, or phenyl;

$R_{10}$ is H, $C_1$–$C_{17}$alkyl, $C_1$–$C_{12}$alkoxy, phenoxy, phenyl, $C_7$–$C_{11}$phenylalkyl, cyclohexyl, $C_7$–$C_{11}$ cyclohexylalkyl, norbornyl, norbornenyl, 1-adamantyl or phenyl-NH—;

$R_{16}$ is hydrogen or is as defined for $R_6$; and $R_{18}$ is $C_3$–$C_{10}$alkylene.

Particular preference is given to novel compositions in which, in the compound of the formula I, $R_6$ is $C_1$–$C_{16}$alkyl;

$R_8$ is $C_1$–$C_{18}$alkyl, $C_3$alkenyl, cyclohexyl, methylcyclohexyl, phenyl or benzyl and, if Z is a group of the formula II, additionally comprises $C_3$–$C_{13}$alkyl interrupted by O;

$R_9$ is $C_2$–$C_{14}$alkyl or $C_3$–$C_{14}$alkyl interrupted by O, or phenyl;

$R_{10}$ is $C_1$–$C_{17}$alkyl, $C_1$–$C_{12}$alkoxy, phenyl, $C_7$–$C_{11}$phenylalkyl, cyclohexyl or phenyl-NH—;

$R_{16}$ is hydrogen or is as defined for $R_6$; and $R_{18}$ is $C_3$–$C_{10}$alkylene.

Of particular importance are novel compositions in which, in the compound of the formula I, $R_1$, $R_5$, $R_{11}$ and $R_{15}$, independently of one another, are H or $C_1$–$C_4$alkyl;

$R_2$, $R_3$, $R_4$, $R_{12}$, $R_{13}$ and $R_{14}$, independently of one another, are H, $C_1$–$C_4$alkyl, methoxy, phenyl, —F, —Cl, benzyl or —CN;

m is a number from the range 1 to 8;

$R_6$ is $C_1$–$C_{16}$alkyl;

$R_8$ is $C_1$–$C_{15}$alkyl, $C_3$alkenyl, cyclohexyl or phenyl and, if Z is a group of the formula II, additionally comprises $C_3$–$C_{13}$alkyl interrupted by O;

$R_9$ is $C_2$–$C_8$alkyl or $C_3$–$C_{12}$alkyl interrupted by O;

$R_{10}$ is $C_1$–$C_{17}$alkyl, $C_1$–$C_{12}$alkoxy or cyclohexyl;

$R_{16}$ is hydrogen or is as defined for $R_6$; and $R_{18}$ is $C_3$–$C_6$alkylene Especial preference is given to novel compositions in which, in the compound of the formula I, $R_1$, $R_2$, $R_3$, $R_4$, $R_5$, $R_{11}$, $R_{12}$, $R_{13}$, $R_{14}$ and $R_{15}$, independently of one another, are H or methyl;

$R_7$ and $R_{17}$, independently of one another, are a radical of one of the formulae IV, V and VI, in which m is 1;

$R_6$ is $C_1$–$C_8$alkyl;

$R_8$ is $C_1$–$C_{10}$alkyl, and, if Z is a group of the formula II, additionally comprises $C_3$–$C_8$alkyl interrupted by O;

$R_9$ is —CH$_2$—O—$R_{19}$;

$R_{10}$ is $C_1$–$C_{17}$alkyl or $C_2$–$C_8$alkoxy;

$R_{16}$ is hydrogen or $C_1$–$C_8$alkyl;

$R_{18}$ is $C_3$–$C_6$alkylene and $R_{19}$ is $C_2$–$C_{13}$alkyl.

The preparation of compounds of the formula I can be carried out in analogy to one of the methods indicated in EP-A-434,608 or in the publication by H. Brunetti and C. E. Lüithi, Helv. Chim. Acta 55, 1566 (1972), by Friedel-Crafts addition of halotriazines onto corresponding phenols. This can be followed by a further reaction by known methods to give compounds of the formula I in which $R_7$ is other than hydrogen; such reactions and processes are described, for example, in EP-A-434 608, page 15, line 11 to page 17, line 1.

The preparation of the compounds of the formula I is expediently carried out starting from one equivalent of a compound of the formula (A)

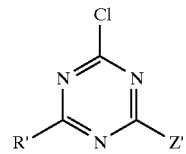

(A)

in which R' is a radical of the formula

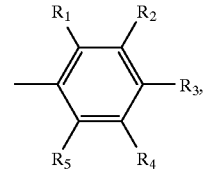

$R_1$, $R_2$, $R_3$, $R_4$ and $R_5$ are each as defined above for formula I and Z' is as defined for R' or is chlorine, and reacting this compound with one (if Z'=R') or two (if Z'=Cl) equivalent(s) of resorcinol.

The reaction is carried out in a manner known per se by reacting the starting materials in an inert solvent in the presence of anhydrous AlCl$_3$. In this reaction, aluminium trichloride and resorcinol are expediently employed in excess; for example, aluminium trichloride can be used in a molar excess of 5–15% and the phenol in a molar excess of 1–30%, especially 5–20%.

Examples of suitable solvents are hydrocarbons, chlorinated hydrocarbons, hydrocarbons containing SO groups or SO$_2$ groups, or nitrated aromatic hydrocarbons: preference is given to high-boiling hydrocarbons such as ligroin, petroleum ether, toluene or xylene, or to sulfolane.

In general the temperature is not critical. It is usual to operate at temperatures between 20° C. and the boiling point of the solvent, for example between 50° C. and 150° C. Working up can be done by customary methods, for example by extraction and separation steps, filtration and drying; if required, it is possible to undertake further purification steps, such as recrystallization for example.

Free phenolic hydroxyl groups of the reaction product that are in the p-position relative to the triazine ring can subsequently be etherified in a known manner.

Thus compounds of the formula I in which $R_7$ and, if desired, $R_{17}$ are a radical of the formula IV

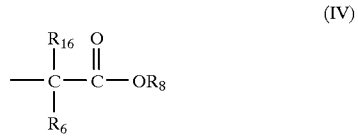
(IV)

can advantageously be prepared by reacting the abovementioned phenolic intermediate with an α-halogenated ester of the formula IV-Hal

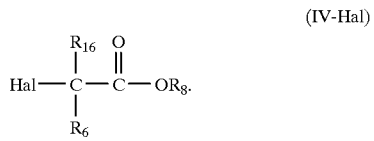
(IV-Hal)

Hal is a halogen atom, for example Cl or Br, preferably Br; the other symbols are as defined above. The reaction is expediently carried out in the presence of an acid-binding agent and an appropriate solvent. It is advantageous to use aprotic solvents such as diglyme, for example. Acid-binding agents which have proven appropriate include carbonates and bicarbonates, for example $K_2CO_3$.

Compounds of the formula I in which $R_7$ and, if desired $R_{17}$ are a radical of the formula V or VI

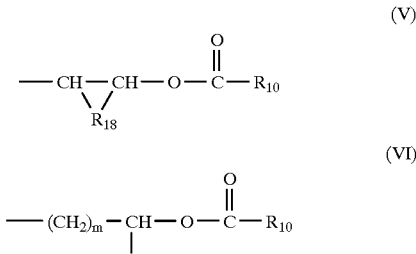
(V)

(VI)

are expediently prepared by way of an alcohol as additional intermediate and subsequent esterification.

For the first reaction step, the preparation of the alcohol, the following methods are among those possible:

i) Reacting the abovementioned phenolic intermediate with a halogenated alcohol of the formula VI-Hal

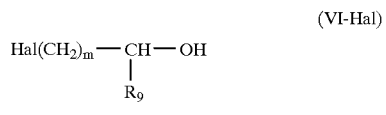
(VI-Hal)

where m in the formula VI-Hal is a number from the range 1–12. Hal is a halogen atom, for example Cl or Br, preferably Br; the remaining symbols are as defined above. The reaction is expediently carried out in the presence of an acid-binding agent and an appropriate solvent, for example diglyme. Acid-binding agents which have proven suitable include hydroxides, carbonates and bicarbonates, for example KOH or $K_2CO_3$.

ii) Reacting the abovementioned phenolic intermediate with an epoxide of one of the formulae V-Ep and VI-Ep

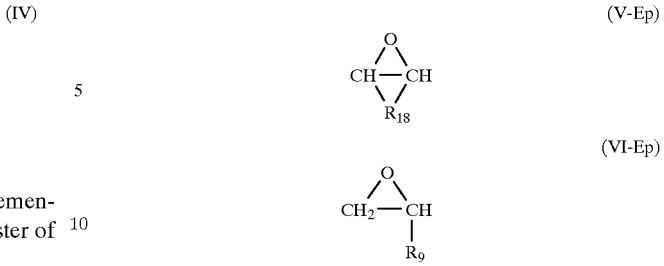
(V-Ep)

(VI-Ep)

The reaction is expediently carried out in the presence of an appropriate catalyst, for example a quaternary ammonium or phosphonium salt, examples being alkyltriphenylphosphonium halides, tetraalkylammonium halides, dialkylphenylammonium hydrohalides. Epoxide VI-EP can, for example, be a glycidyl compound of the formula VI-Gly

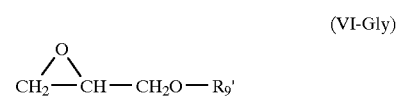
(VI-Gly)

in which $R_9'$ is $C_1$–$C_{11}$ alkyl.

iii) Reacting the abovementioned phenolic intermediate with a carbonate of the formula VI-Cb

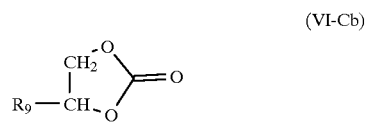
(VI-Cb)

with heating and elimination of $CO_2$. This reaction is also expediently carried out in the presence of appropriate catalysts, examples being quaternary ammonium salts.

The abovementioned reactions often take place with heating to a temperature range of 80–200° C., expediently in the presence of an appropriate solvent, for example an aprotic solvent. For example, reaction ii) can be carried out using triphenylethylphosphonium bromide in mesitylene at 150° C.

The esterification of the aliphatic OH group can be achieved, for example, by reaction with acid chlorides or anhydrides of the formulae V-AC and V-An

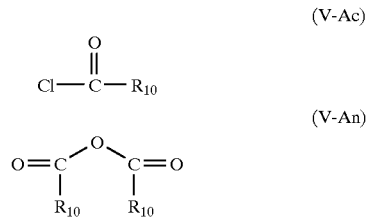
(V-Ac)

(V-An)

expediently using a basic catalyst and an appropriate solvent. It is common to operate at temperatures above 20–25° C., for example in the range 50–150° C. Suitable catalysts include tertiary amines, for example triethylamine or pyridine, preferably using only catalytic amounts of amine. The solvent employed is expediently an apolar aprotic compound, for example a hydrocarbon having an appropriate boiling range, such as toluene or xylene.

Starting compounds of the formula (A) can be prepared, for example, by reacting cyanuric chloride with an appropriately substituted phenylmagnesium halide (Grignard reaction). The reaction can likewise be performed in a known manner, for example in analogy to the process described in EP-A-577,559. This is done by first of all preparing the phenylmagnesium halide by reaction of a compound of the formula

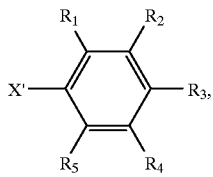

in which X' is Cl oder Br with metallic magnesium in an ether, for example in diethyl ether or in tetrahydrofuran (THF). This reagent is subsequently reacted with cyanuric chloride to form the compound of the formula (A), preferably with exclusion of oxygen and moisture, for example under nitrogen. Subsequent working up can again be carried out in a known manner, for example by dilution with an organic solvent, for example toluene, hydrolysis of residual phenylmagnesium halide with aqueous HCl, and isolation, drying and concentration of the organic phase.

The starting compounds of the formula (A) can also be prepared by Friedel-Crafts reaction of a compound of the formula

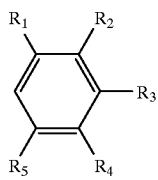

with $AlCl_3$ and cyanuric chloride, for example in analogy to the process described in GB-A-884,802.

The compounds of the formula I are mostly novel compounds. The invention therefore also provides a compound of the formula I'

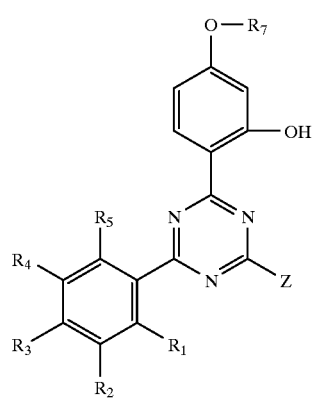

(I')

in which Z is a group of the formula II'

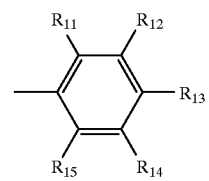

(II')

or a group of the formula III'

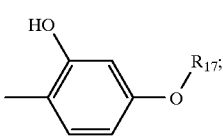

(III')

$R_1$, $R_5$, $R_{11}$ and $R_{15}$, independently of one another, are H, $C_1$–$C_{12}$alkyl, $C_3$–$C_6$alkenyl, $C_1$–$C_{12}$alkoxy, $C_3$–$C_6$alkenoxy, halogen or —CN;

$R_2$, $R_3$, $R_4$, $R_{12}$, $R_{13}$ and $R_{14}$, independently of one another, are H, $C_1$–$C_{12}$alkyl, $C_2$–$C_6$alkenyl, $C_1$–$C_{12}$alkoxy, $C_3$–$C_6$alkenoxy, phenyl, halogen, trifluoromethyl; $C_7$–$C_{11}$ phenylalkyl; phenyloxy; or —CN;

$R_7$ and $R_{17}$, independently of one another, are a radical of one of the formulae IV', V'and VI'

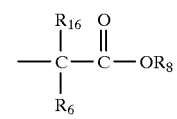

(IV')

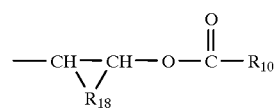

(V')

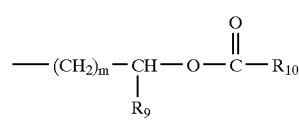

(VI')

in which m is a number from the range 1 to 12;
$R_6$ is $C_1$–$C_{16}$alkyl, —$COOR_8$ or phenyl;
$R_8$ is H, $C_1$–$C_{18}$alkyl, $C_3$–$C_{18}$alkenyl, $C_5$–$C_{12}$cycloalkyl, $C_1$–$C_4$alkylcyclohexyl, phenyl, $C_7$–$C_{14}$alkylphenyl, $C_6$–$C_{15}$bicycloalkyl, $C_6$–$C_{15}$-bicycloalkenyl, $C_6$–$C_{15}$tricycloalkyl, $C_6$–$C_{15}$bicycloalkyl-alkyl or $C_7$–$C_{11}$phenylalkyl, and, if Z is a group of the formula II, additionally comprises $C_2$–$C_{18}$alkyl interrupted by O;
$R_9$ is $C_2$–$C_{14}$alkyl or phenyl; or is $C_1$–$C_{14}$alkyl which is substituted by phenyl, phenoxy, $C_1$–$C_4$alkylcyclohexyl, $C_1$–$C_4$alkylcyclohexyloxy, $C_5$–$C_{12}$cycloalkyl or $C_5$–$C_{12}$cycloalkoxy;
$R_{10}$ is H, $C_1$–$C_{17}$alkyl, $C_1$–$C_{12}$alkoxy, phenoxy, phenyl, $C_7$–$C_{11}$phenylalkyl, $C_7$–$C_{14}$alkylphenoxy, $C_7$–$C_{11}$phenylalkoxy, $C_6$–$C_{12}$cycloalkyl, $C_1$–$C_4$alkylcyclohexyloxy, $C_6$–$C_{12}$cycloalkoxy, $C_7$–$C_{11}$cyclohexylalkyl, $C_7$–$C_{11}$cyclohexylalkoxy, $C_6$–$C_{15}$bicycloalkyl, $C_6$–$C_{15}$bicycloalkenyl, $C_6$–$C_{15}$tricycloalkyl, $C_6$–$C_{15}$bicycloalkoxy, $C_6$–$C_{15}$bicycloalkenoxy, $C_6$–$C_{15}$tricycloalkoxy or phenyl-NH—;

$R_{16}$ is as defined for $R_6$ and, if Z is a group of the formula II, additionally comprises hydrogen; and $R_{18}$ is $C_3$–$C_{10}$alkylene, with the exception of those compounds in which Z is a group of the formula III and $R_1$ and $R_5$ are both alkyl, and of those in which $R_3$ or $R_{13}$ is phenyl and $R_7$ or $R_{17}$ is a radical of the formula VI' or $R_{16}$ is hydrogen.

Preferred novel compounds are, within the scope of the definitions given for formula I', the same as indicated earlier above for formula I; of corresponding interest are, furthermore, novel compounds of the formula I' in which $R_1$, $R_5$, $R_{11}$, and $R_{15}$, independently of one another, are H, $C_1$–$C_4$alkyl, $C_3$alkenyl, $C_1$–$C_4$alkoxy, $C_3$–$C_6$alkenoxy, —F or —Cl;

$R_2$, $R_3$, $R_4$, $R_{12}$, $R_{13}$ and $R_{14}$, independently of one another, are H, $C_1$–$C_4$alkyl, $C_3$–$C_6$alkenyl, $C_1$–$C_4$alkoxy, $C_3$–$C_6$alkenoxy, phenyl, —F, —Cl, or —CN;

$R_6$ is $C_1$–$C_{16}$alkyl or phenyl;

$R_8$ is H, $C_1$–$C_8$alkyl, $C_3$–$C_{18}$alkenyl, cyclohexyl, $C_1$–$C_4$alkylcyclohexyl, phenyl, or $C_7$–$C_{11}$phenylalkyl and, if Z is a group of the formula II, additionally comprises $C_2$–$C_{18}$alkyl interrupted by O;

$R_9$ is $C_2$–$C_{14}$alkyl;

$R_{10}$ is H, $C_1$–$C_{17}$alkyl, $C_1$–$C_{12}$alkoxy, phenoxy, phenyl, $C_7$–$C_{11}$phenylalkyl, cyclohexyl, $C_7$–$C_{11}$cyclohexylalkyl, or phenyl-NH—;

$R_{16}$ is as defined for $R_6$; and, if Z is a group of the formula II, additionally comprises hydrogen; and $R_{18}$ is $C_3$–$C_{10}$alkylene.

Particular preference is given to novel compounds of the formula I' in which $R_6$ is $C_1$–$C_{16}$alkyl;

$R_8$ is $C_1$–$C_{18}$alkyl, $C_3$alkenyl, cyclohexyl, phenyl or benzyl and, if Z is a group of the formula II, additionally comprises $C_3$–$C_{13}$alkyl interrupted by O;

$R_{10}$ is $C_1$–$C_{17}$alkyl, $C_1$–$C_{12}$alkoxy, phenyl, $C_7$–$C_{11}$phenylalkyl, cyclohexyl or phenyl-NH—; and $R_{18}$ is $C_3$–$C_6$alkylene.

Of particular importance are novel compounds of the formula I' in which $R_1$, $R_5$, $R_{11}$ and $R_{15}$, independently of one another, are H or $C_1$–$C_4$alkyl;

$R_2$, $R_3$, $R_4$, $R_{12}$, $R_{13}$ and $R_{14}$, independently of one another, are H, $C_1$–$C_4$alkyl, methoxy, phenyl, —F, —Cl, benzyl or —CN;

m is a number from the range 1 to 8;

$R_6$ is $C_1$–$C_{16}$alkyl;

$R_8$ is $C_1$–$C_{15}$alkyl, $C_3$alkenyl, cyclohexyl or phenyl and, if Z is a group of the formula II, additionally comprises $C_3$–$C_{13}$alkyl interrupted by O;

$R_9$ is $C_2$–$C_8$alkyl;

$R_{10}$ is $C_1$–$C_{17}$alkyl, $C_1$–$C_{12}$alkoxy or cyclohexyl and $R_{18}$ is $C_3$–$C_6$alkylene;

especially those in which $R_1$, $R_3$, $R_{11}$ and $R_{13}$, independently of one another, are H or methyl; and $R_2$, $R_4$, $R_5$, $R_{12}$, $R_{14}$ and $R_{15}$ are H;

$R_7$ and $R_{17}$, independently of one another, are a radical of one of the formulae IV, V and VI, in which m is 1;

$R_6$ is $C_1$–$C_8$alkyl;

$R_8$ is $C_1$–$C_{10}$alkyl, and, if Z is a group of the formula II, additionally comprises $C_3$–$C_8$alkyl interrupted by O;

$R_9$ is $C_2$–$C_8$alkyl;

$R_{10}$ is $C_1$–$C_{17}$alkyl or $C_2$–$C_8$alkoxy and $R_{18}$ is $C_3$–$C_6$alkylene.

The invention additionally provides compositions comprising

A) an organic material which is sensitive to the action of light, oxygen and/or heat, and B) as stabilizer, a compound of the formula I', and a process for stabilizing organic material against the action of light, oxygen and/or heat, which comprises admixing to this material a compound of the formula I' as stabilizer, and provides for the use of a compound of the formula I' as a stabilizer against the action of light, oxygen and/or heat.

Possible examples of such materials to be stabilized in accordance with the invention by adding a compound of the formula I' are oils, fats, waxes, photographic material, cosmetics or biocides. Of particular interest is their use in polymeric materials, as present in plastics, rubbers, coating materials or adhesives. Where the material to be stabilized comprises photographic material, its structure is preferably as described in the U.S. Pat. No. 5,538,840 from column 25, line 60, to column 106, line 35, and the novel compound of the formula I is applied analogously to the application of the compound of the formula (I) described in U.S. Pat. No. 5,538,840 and/or polymers prepared therefrom; the sections mentioned of U.S. Pat. No. 5,538,840 are hereby incorporated by reference.

The following compounds are examples of compounds of the formula I; the suffix n in each case denotes a straight-chain radical, the suffix i a mixture of different isomeric radicals:

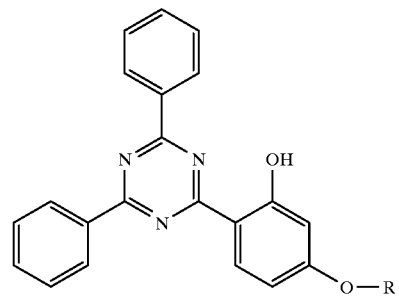

(1) R=CH(CH$_3$)—CO—O—CH$_3$
(2) R=CH(CH$_3$)—CO—O—C$_2$H$_5$
(3) R=CH(C$_2$H$_5$)—CO—O—C$_8$H$_{17}$
(4) R=CH(C$_2$H$_5$)—CO—O—CH$_2$CH$_2$—O—C$_2$H$_5$
(5) R=CH(C$_3$H$_7$-n)—CO—O—C$_8$H$_{17}$
(6) R=CH(C$_4$H$_9$-n)—CO—O—C$_8$H$_{17}$
(7) R=CH(C$_6$H$_{13}$-n)—CO—O—C$_2$H$_5$
(8) R=CH(C$_6$H$_{13}$-n)—CO—O—CH$_2$—CH(CH$_3$)$_2$
(9) R=CH(C$_6$H$_{13}$-n)—CO—O—C$_8$H$_{17}$-i
(10) R=CH(C$_6$H$_{13}$-n)—CO—O—CH$_2$—CH(C$_2$H$_5$)$_2$
(11) R=CH(C$_6$H$_{13}$-n)—CO—O—CH$_2$CH$_2$—O—C$_2$H$_5$
(12) R=CH$_2$—CH(CH$_2$—O—C$_4$H$_9$-n)—O—CO—CH$_3$
(13) R=CH$_2$—CH(CH$_2$—O—C$_4$H$_9$-n)—O—CO—C(CH$_3$)$_3$
(14) R=CH$_2$—CH(CH$_2$—O—C$_4$H$_9$-n)—O—CO—C$_{11}$H$_{23}$-n

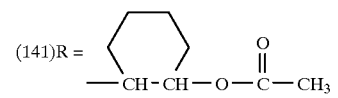

(141) R =

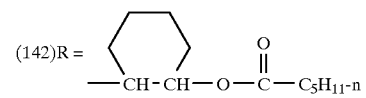

(142) R =

-continued

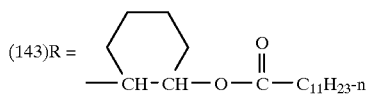

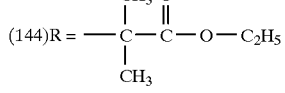

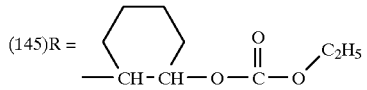

(146) R = CH₂—CH(CH₂—O—C₄H₉-n)—O—CO—O—C₂H₅
(147) R = CH₂—CH(CH₂—O—C₄H₉-n)—O—CO—O—C₄H₉-n

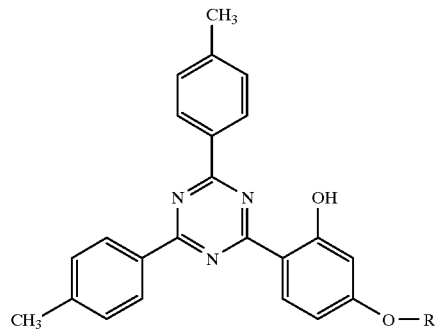

(15) R=CH(CH₃)—CO—O—C₂H₅
(16) R=CH(C₂H₅)—CO—O—C₈H₁₇
(17) R=CH(C₃H₇-n)—CO—O—C₈H₁₇
(18) R=CH(C₄H₉-n)—CO—O—C₈H₁₇
(19) R=CH(C₆H₁₃-n)—CO—O—C₂H₅
(20) R=CH(C₆H₁₃-n)—CO—O—C₈H₁₇-i
(21) R=CH(C₆H₁₃-n)—CO—O—CH₂—CH(C₂H₅)₂
(22) R=CH(C₆H₁₃-n)—CO—O—CH₂CH₂—O—C₂H₅
(23) R=CH₂—CH(CH₂—O—C₄H₉-n)—O—CO—CH₃
(24) R=CH₂—CH(CH₂—O—C₄H₉-n)—O—CO—C(CH₃)₃
(25) R=CH₂—CH(CH₂—O—C₄H₉-n)—O—CO—C₁₁H₂₃-n

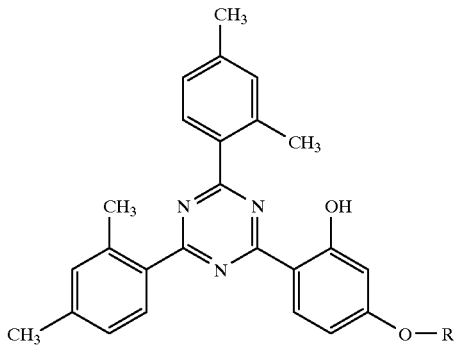

(26) R=CH(CH₃)—CO—O—C₂H₅
(27) R=CH(C₂H₅)—CO—O—C₈H₁₇
(28) R=CH(C₃H₇-n)—CO—O—C₈H₁₇
(29) R=CH(C₄H₉-n)—CO—O—C₈H₁₇
(30) R=CH(C₆H₁₃-n)—CO—O—C₂H₅
(31) R=CH(C₆H₁₃-n)—CO—O—CH₂—CH(CH₃)₂
(32) R=CH(C₆H₁₃-n)—CO—O—C₈H₁₇-i
(33) R=CH(C₆H₁₃-n)—CO—O—CH₂—CH(C₂H₅)₂
(34) R=CH(C₆H₁₃-n)—CO—O—CH₂CH₂—O—C₂H₅

(36) R=CH(C₉H₁₉-n)—CO—O—C₂H₅
(37) R=CH₂—CH(CH₂—O—C₄H₉-n)—O—CO—CH₃
(38) R=CH₂—CH(CH₂—O—C₄H₉-n)—O—CO—C(CH₃)₃
(39) R=CH₂—CH(CH₂—O—C₄H₉-n)—O—CO—C₁₁H₂₃-n

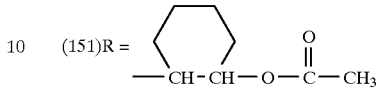

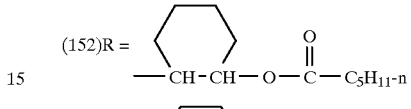

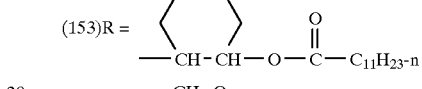

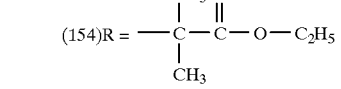

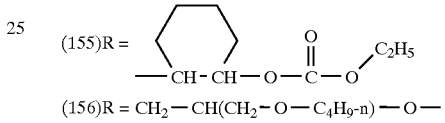

(156) R = CH₂—CH(CH₂—O—C₄H₉-n)—O—CO—O—C₂H₅
(157) R = CH₂—CH(CH₂—O—C₄H₉-n)—O—CO—O—C₄H₉-n

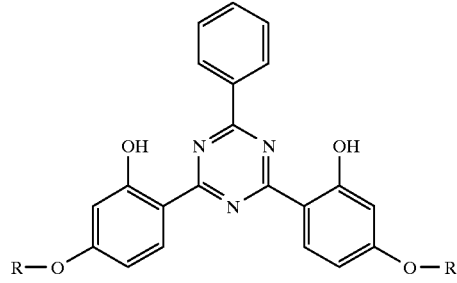

(40) R=CH(CH₃)—CO—O—C₂H₅
(45) R=CH(C₄H₉-n)—CO—O—C₂H₅
(46) R=CH(C₄H₉-n)—CO—O—CH(CH₃)₂
(47) R=CH(C₄H₉-n)—CO—O—C₄H₉-n
(48) R=CH(C₉H₁₉-n)—CO—O—C₂H₅
(52) R=CH₂—CH(CH₂—O—C₄H₉-n)—O—CO—CH₃
(53) R=CH₂—CH(CH₂—O—C₄H₉-n)—O—CO—C(CH₃)₃
(54) R=CH₂—CH(CH₂—O—C₄H₉-n)—O—CO—C₁₁H₂₃-n

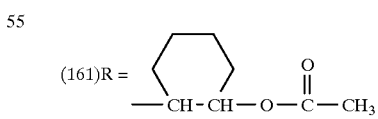

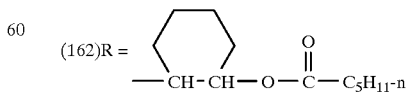

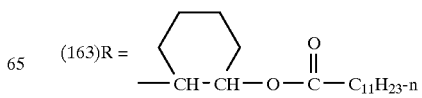

-continued

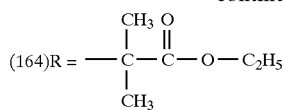

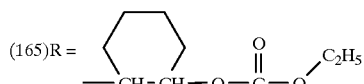

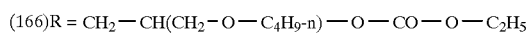

The examples below describe the invention in more detail without constituting a restriction. In the examples, parts and percentages are by weight; if an example mentions room temperature, then this is taken to mean a temperature in the range 20–25° C. In the case of solvent mixtures, for chromatography for example, parts by volume are indicated. These definitions apply in each case unless otherwise stated.

The following abbreviations are used:

| | |
|---|---|
| THF | tetrahydrofuran |
| abs. | anhydrous |
| m.p. | melting point or melting range |
| NMR | nuclear magnetic resonance |
| torr = | mmHg (1 torr corresponds to about 133 Pa) |
| $T_g$ | glass transition temperature |

A) Preparation examples

EXAMPLE A1
2,4-Diphenyl-6-(2-hydroxy-4-[(1-methoxycarbonyl)ethoxy]phenyl)-1,3,5-triazine A suspension of 20.0 g (0.0596 mol) of 2,4-diphenyl-6-(2,4-dihydroxyphenyl)-1,3,5-triazine, 8.1 g (0.0586 mol) of anhydrous $K_2CO_3$ (Merck, 99%) and 0.3 g (1.8 mmol) of potassium iodide (Merck, 99.5%) in 100 ml of diethylene glycol dimethyl ether (diglyme, Fluka, 99.5%) is heated to 60° C. under nitrogen. 10.3 g (61.9 mmol) of methyl 2-bromopropionate (Fluka, 99%) are added. The mixture is heated at 110° C. with stirring for a period of 16 h. Filtration and evaporative concentration of the filtrate on a rotary evaporator give 27.3 g of crude product which following recrystallization from 80 ml of ethylcellosolve (2-ethoxyethanol) and drying for 14 hours at 100° C./60 torr give 18.5 g of title product (compound 1) of the formula

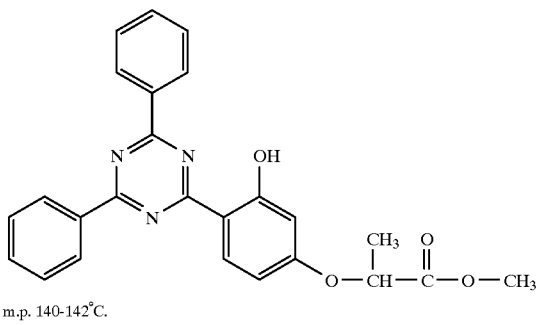

m.p. 140-142°C.

The same method is used to obtain compounds 2–11, 15–22, 26–36 and 40–48 of Table A1 below, the corresponding phenol compound being reacted in each case with the stated halide. In the case of the use of the bisresorcinyl precursor for the compounds 40–51, twice the amount of the halogen compound indicated is used. The crude product is purified either as described above by recrystallization from ethylcellosolve (urification method R) or by column chromatography (silica gel 60, 230–400 mesh, eluted with toluene/ethyl acetate in a volume ratio of 9:1) (purification method C). The melting ranges given for characterization are stated in ° C.; other characterization parameters are noted in the column. The analytical data give the amounts found in % by weight.

TABLE A1

Preparation of the compounds 2–11, 15–22, 26–36 and 40–51

| No. | Starting material | m.p. or characterization | Analysis (found) % C | % H | % N |
|---|---|---|---|---|---|
| (2) | BrCH(CH$_3$)COOC$_2$H$_5$ | 137–140° C. | 70.55 | 5.29 | 9.58 |
| (3) | BrCH(C$_2$H$_5$)COOC$_8$H$_{17}$ | | 73.76 | 7.10 | 7.19 |
| (4) | BrCH(C$_2$H$_5$)COOCH$_2$CH$_2$OC$_2$H$_5$ | 98–104° C. | 69.99 | 5.99 | 8.43 |
| (5) | BrCH(C$_3$H$_7$—n)—CO—O—C$_8$H$_{17}$ | | 74.02 | 6.91 | 7.38 |
| (6) | BrCH(C$_4$H$_9$—n)—CO—O—C$_8$H$_{17}$ | | 74.24 | 7.36 | 6.97 |
| (7) | BrCH(C$_6$H$_{13}$—n)—CO—O—C$_2$H$_5$ | 120–122° C. | 72.99 | 6.37 | 7.87 |
| (8) | BrCH(C$_6$H$_{13}$—n)COOCH$_2$CH(CH$_3$)$_2$ | 87–93° C. | 73 . 64 7.09 | 7.87 | |
| (9) | BrCH(C$_6$H$_{13}$—n)—CO—O—C$_8$H$_{17}$—i | | 74.75 | 7.71 | 6.91 |
| (10) | BrCH(C$_6$H$_{13}$—n)COOCH$_2$CH(C$_2$H$_5$)$_2$ | 79–82° C. | 74. 1 9 7 .25 | 7 .4 1 | |
| (11) | BrCH(C$_6$H$_{13}$—n)COOCH$_2$CH$_2$OC$_2$H$_5$ | 104–109° C. | 71 .6 | 6.82 | 7.41 |
| (15) | BrCH(CH$_3$)—CO—O—C$_2$H$_5$ | | | | |
| (16) | BrCH(C$_2$H$_5$)—CO—O—C$_8$H$_{17}$ | | 74.24 | 7.47 | 6.88 |
| (17) | BrCH(C$_3$H$_7$—n)—CO—O—C$_8$H$_{17}$ | | 74.36 | 7.43 | 7.09 |
| (18) | BrCH(C$_4$H$_9$—n)—CO—O—C$_8$H$_{17}$ | | 74.60 | 7.72 | 6.53 |
| (19) | BrCH(C$_6$H$_{13}$—n)—CO—O—C$_2$H$_5$ | 138–140° C. | 73.30 | 7.00 | 7.72 |
| (20) | BrCH(C$_6$H$_{13}$—n)—CO—O—C$_8$H$_{17}$—i | | 75.27 | 8.15 | 6.28 |
| (21) | BrCH(C$_6$H$_{13}$—n)COOCH$_2$CH(C$_2$H$_5$)$_2$ | 92–94° C. | 74.37 | 7.66 | 6.79 |
| (22) | BrCH(C$_6$H$_{13}$—n)COOCH$_2$CH$_2$OC$_2$H$_5$ | 118–121° C. 71 .78 7.30 | 7.06 | | |

TABLE A1-continued

Preparation of the compounds 2–11, 15–22, 26–36 and 40–51

| | | | Purification | | |
|---|---|---|---|---|---|
| | Starting | m.p. or character- | Analysis (found) | | |
| No. | material | ization | % C | % H | % N |
| (26) | BrCH(CH$_3$)—CO—O—C$_2$H$_5$ | 120–1220C | 72.43 | 6.54 | 8.38 |
| (27) | BrCH(C$_2$H$_5$)—CO—O—C$_8$H$_{17}$ | 74.99 | 7.78 | 6.74 | |
| (28) | BrCH(C$_3$hd 7—n)—CO—O—C$_8$H$_{17}$ | 75.25 | 7.83 | 6.42 | |
| (29) | BrCH(C$_4$H$_9$—n)—CO—O—C$_8$H$_{17}$ | 75.11 | 7.96 | 6.39 | |
| (30) | BrCH(C$_6$H$_{13}$—n)—CO—O—C$_2$H$_5$ | 94–950C | 74.32 | 7.50 | 7.51 |
| (31) | BrCH(C$_6$H$_{13}$—n)COOCH$_2$CH(CH$_3$)$_2$ | 74.60 | 7.82 | 6.77 | |
| (32) | BrCH(C$_6$H$_{13}$—n)—CO—O—C$_8$H$_{17}$—i | 75 .28 | 8.25 | 6.20 | |
| (33) | BrCH(C$_6$H$_{13}$—n)COOCH$_2$CH(C$_2$H$_5$)$_2$ | 75.15 | 7.95 | 6.76 | |
| (34) | BrCH(C$_6$H$_{13}$—n)COOCH$_2$CH$_{2OC_2}$H$_5$ | 87–900C | 72.58 | 7.48 | 6.66 |
| (36) | BrCH(C$_9$H$_{19}$—n)—CO—O—C$_2$H$_5$ | 74.18 | 7.76 | 6.78 | |
| (40) | BrCH(CH$_3$)—CO—O—C$_2$H$_5$ | 131–1450C | 64.63 | 5.47 | 7.07 |
| (45) | BrCH(C$_4$H$_9$—n)—CO—O—C$_2$H$_5$ | 67.03 | 6.83 | 6.05 | |
| (46) | BrCH(C$_4$H$_9$—n)—CO—O—CH(CH$_3$)$_2$ | 68.55 | 6.97 | 6.04 | |
| (47) | BrCH(C$_4$H$_9$—n)—CO—O—C$_4$H$_9$—n | 69.03 | 7.16 | 5.60 | |
| (48) | BrCH(C$_9$H$_{19}$—n)—CO—O—C$_2$H$_5$ | 70.55 | 8.29 | 4.90 | |

Starting material for compounds 37–39 (EP-A-434 608, Example 1) 23.8 g (0.06 mol) of 2-(2,4-dihydroxyphenyl)-4,6-bis(2,4-dimethylphenyl)-1,3,5-triazine (prepared in accordance with U.S. Pat. No. 3,244,708, Example 16) are dispersed in 300 ml of xylene. 12.1 g (0.09 mol) of 97% of butyl glycidyl ether and 0.75 g (0.006 mol) of dimethylbenzylamine are added and the mixture is refluxed. After 5 hours, the brown solution is cooled and filtered through 100 g of silica gel. The yellow solution is concentrated and the residue is recrystallized from hexane/toluene. This gives 27.3 g of 2-[2-hydroxy-4-(3-butoxy-2-hydroxypropyloxy) phenyl]-4,6-bis(2,4-dimethylphenyl)-1,3,5-triazine (=86%) of melting point 80–83° C.

An analogous method is used to obtain the starting materials for compounds 12–14, 23–25 and 52–54, of the formula:

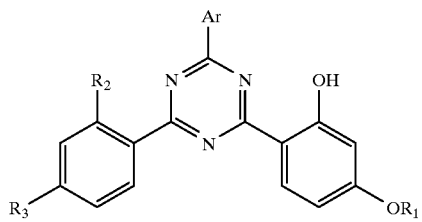

| Starting material for Compd. No. | Ar | R$_2$ | R$_3$ | R$_1$ |
|---|---|---|---|---|
| 12–14 | phenyl | H | H | —CH$_2$—CH(OH)—CH$_2$—O—C$_4$H$_9$-n |
| 23–25 | p-tolyl | H | CH$_3$ | —CH$_2$—CH(OH)—CH$_2$—O—C$_4$H$_9$-n |
| 37–39 | m-xylyl | CH$_3$ | CH$_3$ | —CH$_2$—CH(OH)—CH$_2$—O—C$_4$H$_9$-n |
| 52–54 | phenyl | OH | =OR$_1$ | —CH$_2$—CH(OH)—CH$_2$—O—C$_4$H$_9$-n |

EXAMPLE A2

Compounds 12, 23, 37 and 52

A mixture of 20.0 g (31.6 mmol) of 2-phenyl4,6-bis[2-hydroxy-4-(3-butoxy-2-hydroxypropyloxy)phenyl]-1,3,5-triazine, 7.4 g (94.8 mmol) of acetyl chloride (Fluka, 99%) and 0.8 g (10 mmol) of pyridine in 250 ml of toluene (Fluka, 99.5%) is stirred under nitrogen and maintained at 60° C. for 14 h.

After cooling, the solvent is stripped off on a rotary evaporator and the crude product is purified by column chromatography (silica gel 60, 230–400 mesh; eluted with petroleum ether/ethyl acetate [2:1]). This gives 2-phenyl-4,6-bis[2-hydroxy-4-(3-n-butoxy-2-acetyloxypropoxy)phenyl]-1,3,5-triazine (compound 52) as the main fraction, which is dried at 80° C./0.01 torr for 2 h.

The same method is used to obtain compounds 12, 13 and 37 of Table A2 below, in which the corresponding phenol compound is in each case reacted with the stated halide in a prolonged reaction duration of 70 h. Where monoresorcinyl starting materials are used, half the amount of halogen compound stated is employed. The melting ranges indicated for characterization are stated in ° C.; other characterization parameters are noted in the column.

The analytical data indicate the amounts found in % by weight.

TABLE A2

Characterization of the compounds 12, 23, 37 and 52

| No. | m.p. or characterization | Analysis (found) | | |
|---|---|---|---|---|
| | | % C | % H | % N |
| (12) | 108–110° C. | 70.09 | 6.21 | 8.12 |
| (23) | 104–108° C. | 70.70 | 6.57 | 7.72 |
| (37) | | 71.55 | 7.15 | 6.99 |
| (52) | | 65.13 | 6.65 | 5.71 |

EXAMPLE A3

Compounds 13, 24, 38 and 53

A mixture of 20.0 g (31.6 mnmol) of 2-phenyl-4,6-bis[2-hydroxy-4-(3-butoxy-2-hydroxypropyloxy)phe nyl]-1,3,5-triazine, 16.3 g (135.3 mmol) of pivaloyl chloride (Fluka, 98%) and 0.8 g (10 mmol) of pyridine in 250 ml of toluene (Fluka, 99.5%) is stirred under nitrogen and held at 100° C. for 14 hours. After cooling, solvents and excess starting material are stripped off on a rotary evaporator and the crude product is purified by column chromatography (silica gel 60, 230–400 mesh; column h=4 cm, d=6 cm; eluted withethyl acetate). This gives 2-phenyl-4,6-bis[2-hydroxy-4-(3-n-butoxy-2-pivaloyloxypropoxy )phenyl]-1,3,5-triazine (compound 53) as the main fraction, which is dried at 100° C./0.01 torr for 3 h.

The same method is used to obtain the compounds 13, 24 and 38 of Table A3 below, in which the corresponding phenol compound is in each case reacted with the stated halide. Where monoresorcinyl starting materials are employed, half the amount of halogen compound stated is used. The melting ranges stated for characterization are indicated in ° C.; other characterizing parameters are noted in the column. The analytical data give the amounts found in % by weight.

TABLE A3

Characterization of compounds 13, 24, 38 and 53

| No. | m.p. or characterization | Analysis (found) | | |
|---|---|---|---|---|
| | | % C | % H | % N |
| (13) | | 70.89 | 6.84 | 7.13 |
| (24) | 104–107° C. | 72.12 | 7.10 | 7.23 |
| (38) | | 72.68 | 7.52 | 6.46 |
| (53) | | 67.36 | 7.65 | 5.15 |

EXAMPLE A4

Compounds 14, 25, 39, 166, 167 and 54 and also 162, 163 and 165

A mixture of 14.0 g (22.0 mmol) of 2-phenyl-4,6-bis[2-hydroxy-4-(3-butoxy-2-hydroxypropyloxy)phenyl]-1,3,5-triazine, 10.6 g (48.5 mmol) of dodecanoyl lauric acid chloride (Fluka, 98%) and 0.8 g (10 mmol) of pyridine in 150 ml of toluene (Fluka, 99.5%) is stirred under nitrogen and held at 90–100° C. for 5 hours.

After cooling, the solvent is stripped off on a rotary evaporator and the crude product is purified by column chromatography (silica gel 60, 230–400 mesh; column h=4 cm, d=6 cm; eluted withethyl acetate). This gives 2-phenyl-4,6-bis[2-hydroxy-4-(3-n-butoxy-2-dodecanoyloxypropoxy)phenyl]-1,3,5-triazine (compound 54) as the main fraction, which is dried at 100° C./0.01 torr for 3 h.

The same method is used to obtain the compounds 14, 25, 39, 54, 166 and 167 of Table A4 below, in which the corresponding phenol compound is in each case reacted with the appropriate halide. Compounds 162, 163 and 165 are prepared by reacting the starting material described below in Example A5c with the appropriate halide. Where monoresorcinyl starting materials are employed, half the amount of halogen compound stated is used. The melting ranges stated for characterization are indicated in ° C.; other characterizing parameters are noted in the column. The analytical data give the amounts found in % by weight.

TABLE A4

Characterization of compounds 14, 25, 39, 162, 163, 165, 166, 167 and 54

| No. | m.p. or characterization | Analysis (found) | | |
|---|---|---|---|---|
| | | % C | % H | % N |
| (14) | | 74.17 | 8.42 | 5.52 |
| (25) | | 73.97 | 8.11 | 6.01 |
| (39) | | 74.45 | 8.40 | 5.50 |
| (54) | | 71.28 | 8.76 | 4.00 |
| (162) | Tg = 10.7° C. | 70.67 | 7.38 | 5.18 |
| (163) | Tg = –8.5° C. | 73.33 | 8.69 | 4.22 |
| (165) | m.p. 57.1° C. (DSC) | 66.67 | 6.37 | 6.00 |
| (166) | Tg = 0.6° C. | 63.37 | 6.64 | 5.22 |
| (167) | Tg = –7.8° C. | 65.28 | 7.10 | 5.02 |

EXAMPLE A5 a) Starting material for compounds 141, 142, 143, 145:

2,4-Diphenyl-6-(2'-hydroxy-4'-(2"-hydroxycyclohexyloxy)phenyl)-1,3,5-triazine Under nitrogen, a mixture of 13.0 g (29.6 mmol) of 2,4-diphenyl-6-(2',4'-dihydroxyphenyl)-1,3,5-triazine, 7.50 g (76.4 mmol) of cyclohexene oxide (Fluka, 99%) and 2.2 g (5.9 mmol) of ethyltriphenylphosphonium bromide (Fluka, 97%) in 65 ml of toluene (Merck, 99.5%) are held at 100° C. with stirring for 42 hours. The orange-coloured solution is filtered at 80° C. After cooling to 0° C. for two hours, the solid is filtered off and dried at 80° C./50 torr for 14 h, to give 10.1 g (77.8%) of the title product of melting point 169–171° C.

b) Starting material for compounds 151, 152, 153, 155:

2,4-Bis(2',4'-dimethylphenyl)-6-(2'-hydroxy-4'-(2"-hydroxycyclohexyloxy)phenyl)-1,3,5-triazine Procedure as under a) using the equivalent amount of 2,4-bis(2',4'-dimethylphenyl)-6-(2',4'-dihydroxyphenyl)-1,3,5-triazine instead of 2,4-diphenyl-6-(2',4'-dihydroxyphenyl)-1,3,5-triazine gives the title product, following recrystallization from toluene, of melting point 160–161° C.

c) Starting material for compounds 161, 162, 163, 165:

2-Phenyl-4,6-bis(2'-hydroxy-4'-(2"-hydroxycyclohexyloxy)phenyl)-1,3,5-triazine Procedure as under a) with 24-hour reaction of 1 equivalent of 2-phenyl-4,6-bis(2',4'-dihydroxyphenyl)-1,3,5-triazine with 3 equivalents of cyclohexene oxide in the presence of 0.1 equivalent of ethyltriphenylphosphonium bromide in mesitylene at 130° C. gives the title product of melting point 137–143° C.

EXAMPLE A6

2,4-Diphenyl-6-(2'-hydroxy-4'-(2"-acetoxycyclohexyloxy) phenyl)-1,3,5-triazine (compound 141)

A mixture of 13.0 g (29.6 mmol) of 2,4-diphenyl-6-(2'-hydroxy4'-(2"-hydroxycyclohexyloxy)phenyl)-1,3,5-triazine, 7.0 g (89.2 mmol) of acetyl chloride (Fluka, 99%) and 0.6 g (7.6 mmol) of pyridine in 140 ml of toluene (Merck, 99.5%) is stirred under nitrogen and held at 50° C. for 6 h.

After cooling, 5.0 g of bleaching earth (Tonsil AC®) are added, the mixture is stirred for 15 minutes, and the bleaching earth is filtered off. The solvent is stripped off on a rotary evaporator and the product is dried at 130° C./0.1 torr for 8 h, to give 13.3 g (93.6%) of the title product; $T_g$=60.4° C. (DSC).

Using the same method and the corresponding starting materials (see Example A5, b and c), compounds 151 and 161 of Table A6 below are obtained. The melting ranges indicated for characterization are stated in ° C.; other characterizing parameters are noted in the column. The analytical data give the amounts found in % by weight.

TABLE A6

Characterization of the compounds 151 and 161

| No. | m.p. or characterization | Analysis (found) | | |
|---|---|---|---|---|
| | | % C | % H | % N |
| (151) | Tg = 389° C. (DSC) | 73.89 | 6.55 | 7.74 |
| (161) | Tg = 58.1° C. | 68.08 | 6.28 | 6.25 |

EXAMPLE A7
2,4-Diphenyl-6-(2'-hydroxy-4'-(2"-dodecanoyloxycyclohexyloxy)phenyl)-1,3,5-triazine (compound 143)

A mixture of 5.0 g (11.3 mmol) of 2,4-diphenyl-6-(2'-hydroxy-4'-(2"-hydroxycyclohexyloxy)phenyl)-1,3,5-triazine, 5.7 g (26 mmol) of dodecanoyl chloride (Fluka, 98%) and 0.1 g (1.3 mmol) of pyridine in 60 ml of toluene is stirred under nitrogen and kept at 50° C. for 20 h.

After cooling, 5.0 g of bleaching earth (Prolith Rapid®) are added, the mixture is stirred for 3 minutes and the bleaching earth is filtered off. The filtrate is concentrated by evaporation and dried. 10.6 g of crude product are recrystallized from 100 ml of hexane. After drying at 60° C./50 torr for 14 h, 5.6 g of the title product are obtained; m.p. 82–95° C.

Using the same method and the corresponding halides, compounds 142, 145, 146 and 147 of Table A7 below are obtained. Using the starting material from Example A5b, the indicated compounds 152, 153, 155, 156 and 157 are obtained. Purification is carried out in some cases by recrystallization from hexane and in some cases by column chromatography. The melting ranges indicated for characterization are in ° C.; other characterizing parameters are noted in the column. The analytical data give the amounts found in % by weight.

TABLE A7

Characterization of compounds 142, 145, 146, 147, 152, 153, 155, 156 and 157

| No. | m.p. or characterization | Analysis (found) | | |
|---|---|---|---|---|
| | | % C | % H | % N |
| (142) | $T_g$ = 38.9° C. (DSC) | 73.64 | 6.46 | 7.77 |
| (145) | m.p. 140–142° C. (DSC) | 70.59 | 5.80 | 8.41 |
| (146) | $T_g$ = 56.0° C. (DSC) | 68.54 | 6.25 | 7.61 |
| (147) | $T_g$ = 55.3° C. (DSC) | 69.52 | 6.57 | 7.27 |
| (152) | UV(CHCl$_3$):ε(339nm) = 24 330 | 74.73 | 7.54 | 7.10 |
| (153) | $T_g$ = -2.8° C. | 76.21 | 8.29 | 6.36 |
| (155) | $T_g$ = 52° C. | 72.10 | 6.75 | 7.35 |
| (156) | $T_g$ = 5.5° C. (DSC) | 70.12 | 6.81 | 7.02 |
| (157) | $T_g$ = 42.2° C. | 70.90 | 7.04 | 6.68 |

EXAMPLE A8
2,4-Diphenyl-6-(2'-hydroxy-4'-(2"-ethoxycarbonylprop-2"-yloxy)phenyl)-1,3,5-triazine (compound 144)

A mixture of 12.7 g (37.2 mmol) of 2,4-diphenyl-6-(2', 4'-dihydroxyphenyl)-1,3,5-triazine, 12.0 g (61.5 mmol) of ethyl α-bromoisobutanoate (Fluka, 97%), 10.3 g (74.5 mmol) of anhydrous potassium carbonate (Merck, 99%) and 0.3 g (2 mmol) of potassium iodide in 60 ml of toluene and 80 ml of diethylene glycol dimethyl ether (Diglyme, Fluka 99.5%) is stirred under nitrogen and held at 100–110° C. for 30 h. It is filtered at 80° C. Evaporation of the filtrate by concentration gives 14.0 g of crude product. After column chromatography (250 g of silica gel 60/230–400 mesh; eluent: toluene/hexane 1:1) the main fraction is dried at 50° C./50 torr for 24 h, giving 9.8 g of the title product; m.p. 131–132° C.

Using the same method and the corresponding starting materials from Example A5 in the appropriate amounts, compounds 154 and 164 indicated in Table A8 are obtained. The melting ranges indicated for characterization are in ° C.; other characterizing parameters are noted in the column. The analytical data give the amounts found in % by weight.

TABLE A8

Characterization of compounds 154 and 164

| No. | m.p. or characterization | Analysis (found) | | |
|---|---|---|---|---|
| | | % C | % H | % N |
| (154) | $T_g$ = 22.3° C. | 72.56 | 6.51 | 8.13 |
| (164) | $T_g$ = 28.1° C. | 65.95 | 5.67 | 7.05 |

B) Use Examples

EXAMPLE B1
Stabilization of a 2-coat metallic system

The compound to be tested is incorporated into 5–10 g of xylene and tested in a clearcoat having the following composition (parts by weight):

| | |
|---|---|
| Uracron ® 2263B[1)] | 59.2 |
| Cymel ® 327[2)] | 11.6 |
| Xylene | 19.4 |
| Butylglycol acetate | 5.5 |
| Butanol | 3.3 |
| Levelling assistant Baysilon ® A[6)] | 1.0 |
| Aluminum trisacetylacetonate (curing catalyst) | 1.6 |
| | 101.6 |

[1)]Acrylate resin, DSM Resins NV
[2)]Melamine resin, American Cyanamide Corp.
[6)]Manufacturer: Bayer AG; 1% solution in xylene To the clearcoat there are added 1.5% by weight of the compound to be tested and also 0.7% of the compound

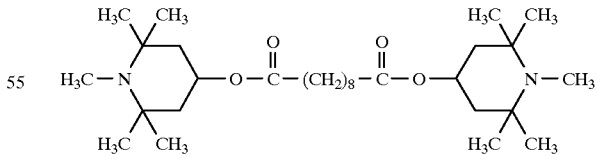

(Compound A), based in each case on the solids content of the coating material. The control used is a clearcoat containing no light stabilizer.

The clearcoat is diluted to spray viscosity with Solvesso® 100 and applied by spraying to a prepared aluminium panel (coil coat, surfacer, silver-metallic basecoat) and stoved at 130° C. for 30 minutes. This gives a dry film thickness of 40–50 μm clearcoat.

The samples are then weathered in an UVCON® weathering instrument from Atlas Corp. (UVB-313 lamps) with a cycle of 8 h UV irradiation at 70° C. and 4 h condensation at 50°C.

The samples are inspected at regular intervals for gloss (20° gloss in accordance with DIN 67530) and freedom from cracks. The results are set out in Table B1 below.

TABLE B1

20° gloss and cracking after the stated period of UVCON weathering

| Stabilizer | Cracking after | 20° gloss | | | | |
|---|---|---|---|---|---|---|
| | | 0 h | 1200 h | 7200 h | 8400 h | 10000 h |
| none | 2000 h | 87 | 48 | | | |
| Compd. No. 5 | 10000 h | 87 | 85 | 68 | 70 | 67 |
| Compd. No. 28 | 10000 h | 87 | 85 | 67 | 62 | 53 |
| Compd. No. 3 | 10000 h | 87 | 83 | 73 | 69 | 68 |
| Compd. No. 16 | 10000 h | 87 | 84 | 71 | 69 | 67 |
| Compd. No. 27 | 10000 h | 87 | 84 | 67 | 61 | 53 |
| Compd. No. 7 | 10000 h | 87 | 81 | 72 | 72 | 70 |
| Compd. No. 19 | 10000 h | 87 | 79 | 74 | 72 | 71 |
| Compd. No. 30 | 10000 h | 87 | 76 | 68 | 62 | 56 |

The samples stabilized in accordance with the invention exhibit better weathering stability (gloss retention, cracking strength) than the unstabilized control sample.

EXAMPLE B2
Stabilization of a powder coating

The compound to be tested is tested in a clearcoat based on a glycidyl methacrylate-functionalized polyacrylate. To this end the following components are mixed in a mixer and extruded twice using a Buss PLK46L cokneader at 40° C. and 80° C. in zones 1 and 2 and 125 revolutions/minute:

| | |
|---|---|
| Synthacryl ® VSC 1436[1] | 756 g |
| Additol ® VXL 1381[1] | 236 g |
| Benzoin | 3 g |
| Additol ® XL 490[2] | 5 g |
| Stabilizer B[3] | 10 g |
| | 1010 g |

[1]Hoechst AG;
[2]Vianova AG;
[3]Di(1,2,2,6,6-pentamethylpiperidin-4-yl) (3,5-di-t-butyl-4-hydroxybenzyl)-n-butyl malonate In addition to the amounts stated, the mixture contains 20 g of the novel stabilizer given in Tab. B2. A further formulation is prepared as indicated but without novel stabilizer.

The extrudate is cooled, conminuted, ground to stage 1 in a Retsch ZM-1 ultracentrifugal mill and with a 1.0 mm sieve, and finally passed through a 90 μm rotary sieve. The resulting powder has a mean particle size of 31 μm.

Test panels of coil-coated aluminium are prepared by applying a coat (35–40 μm) of a water-based primer, followed by a coat of a silver-metallic primer. The surfaces of the test panels are cured at 130° C. for 30 minutes. The clearcoat is then applied using an instrument of type ESB-Wagner® corona gun and cured at 145° C. for 30 minutes. The resulting film thickness is about 60 μm clearcoat.

The samples are then weathered in an UVCON® weathering instrument from Atlas Corp. (UVB-313 nm lamps) with a cycle of 8 h UV irradiation at 70° C. and 4 h condensation at 50° C. The samples are examined for cracking every 400 hours; cracks are assessed in accordance with the TNO scale type 353.

The results are given in Table B2.

TABLE B2

Weathering period of powder coating up to cracking, and assessment in accordance with TNO

| Stabilization | Duration | TNO evaluation |
|---|---|---|
| none | 2800 h | E4b |
| Compound (21) | >10000 h | no cracking |

The samples stabilized in accordance with the invention exhibit a better weathering stability than the unstabilized control sample.

EXAMPLE B3
Stabilization of a 2-coat metallic system

The compound to be tested is incorporated into 5–10 g of xylene and tested in a clearcoat having the following composition (parts by weight):

| | |
|---|---|
| Synthacryl ® SC 303[1] | 31.84 |
| Synthacryl ® SC 370[2] | 23.34 |
| Maprenal ® MF 650[3] | 27.29 |
| Isobutanol | 4.87 |
| Solvesso ® 150[4] | 2.72 |
| Kristallöl K-30[5] | 8.74 |
| Levelling assistant Baysilon ® MA[6] | 1.20 |
| | 100.00 |

[1]Acrylate resin, Hoechst AG; 65% solution in xylene/butanol 26:9
[2]Acrylate resin, Hoechst AG; 75% solution in Solvesso ® 100[4]
[3]Melamine resin, Hoechst AG; 55% solution in isobutanol
[4]Mixture of aromatic hydrocarbons, boiling range 182–203° C. (Solvesso ® 150) or 161–178° C. (Solvesso ® 100); manufacturer: ESSO
[5]Mixture of aliphatic hydrocarbons, boiling range 145–200° C.; manufacturer: Shell
[6]1% in Solvesso ® 150[4] manufacturer: Bayer AG To the clearcoat there are added 1.5% of the compound to be tested and also 0.7% of the compound A (see Example B1), based on the solids content of the coating material. The control used is a clearcoat containing no light stabilizer.

The clearcoat is diluted to spray viscosity with Solvesso® 100 and applied by spraying to a prepared aluminium panel (coil coat, surfacer, silver-metallic basecoat) and stoved at 130° C. for 30 minutes. The result is a dry film thickness of 40–50 μm clearcoat.

The samples are weathered and assessed as described in Example B1. The results are set out in Table B3 below.

TABLE B3

20° gloss and cracking after the stated period of UVCON weathering

| Stabilizer | Cracking after | 20° gloss | | | | |
|---|---|---|---|---|---|---|
| | | 0 h | 1200 h | 2000 h | 2400 h | 2800 h |
| none | 1200 h | 90 | 5 | | | |
| Compd. No. 29 | 2800 h | 90 | 88 | 89 | 73 | 47 |
| Compd. No. 11 | 2800 h | 90 | 86 | 85 | 68 | 30 |
| Compd. No. 34 | 2800 h | 90 | 80 | | | |
| Compd. No. 33 | 2800 h | 90 | | | | |

EXAMPLE B4
A clearcoat is prepared, applied and weathered as described in Example B3.

The results are set out in Table B4 below.

TABLE B4

20° gloss and cracking after the stated period of UVCON weathering

| Stabilizer | Cracking after | 20°-Glanz | | |
|---|---|---|---|---|
| | | 0 h | 1200 h | 2400 h | 2800 h |
| none | 1200 h | 89 | 11 | | |
| Compd. No. 53 | 3200 h | 89 | 89 | 88 | 82 |
| Compd. No. 54 | 3200 h | 88 | 89 | 88 | 68 |
| Compd. No. 23 | 3200 h | 89 | 91 | 90 | 77 |
| Compd. No. 37 | 3200 h | 89 | 91 | 87 | 69 |
| Compd. No. 38 | 3200 h | 89 | 88 | 89 | 60 |
| Compd. No. 24 | 3200 h | 90 | 91 | 89 | |
| Compd. No. 25 | 3200 h | 90 | 91 | 89 | |
| Compd. No. 12 | 3200 h | 90 | 91 | 88 | |
| Compd. No. 13 | 3200 h | 89 | 91 | 90 | |
| Compd. No. 14 | 3200 h | 90 | 90 | 87 | |
| Compd. No. 39 | 3200 h | 90 | 91 | | |

EXAMPLE B5

The procedure of Example B3 is repeated, but the clearcoat contains, instead of 0.7% of compound A, 1.0% by weight of a compound of the formula

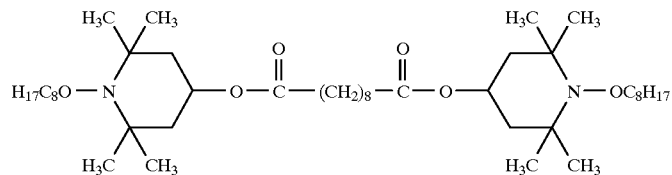

(compound B), and the coating material is applied to light green metallic basecoat. The results are set out in Table B5 below.

TABLE B5

20° gloss and weathering after the stated period of UVCON weathering

| Stabilizer | Cracking after | 20° gloss | | | |
|---|---|---|---|---|---|
| | | 0 h | 0800 h | 4800 h | 5600 |
| none | 1200 h | 83 | 27 | | |
| Compd. No. 9 | 5200 h | 82 | 84 | 74 | |
| Compd. No. 20 | 6000 h | 79 | 87 | 74 | 56 |
| Compd. No. 32 | 5200 h | 82 | 85 | 74 | |

What is claimed is:

1. A composition comprising

A) a synthetic organic polymer or prepolymer and

B) as stabilizer against the damaging effect of light, oxygen and/or heat, a compound of the formula I

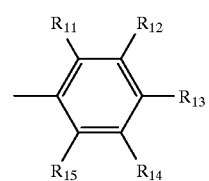

(I)

in which Z is a group of the formula II

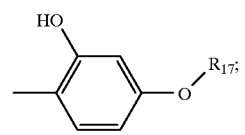

(II)

or a group of the formula III (III)

$R_1$, $R_5$, $R_{11}$ and $R_{15}$, independently of one another, are H, $C_1$–$C_{12}$alkyl, $C_3$–$C_6$alkenyl, $C_1$–$C_{12}$alkoxy, $C_3$–$C_6$alkenoxy, halogen or —CN; $R_2$, $R_3$, $R_4$, $R_{12}$, $R_{13}$ and $R_{14}$, independently of one another, are H, $C_1$–$C_{12}$alkyl, $C_2$–$C_6$alkenyl, $C_1$–$C_{12}$alkoxy, $C_3$–$C_6$alkenoxy, phenyl, halogen, trifluoromethyl, $C_7$–$C_{11}$phenylalkyl, phenyloxy, or —CN;

$R_7$ and $R_{17}$, independently of one another, are a radical of one of the formulae IV, V and VI

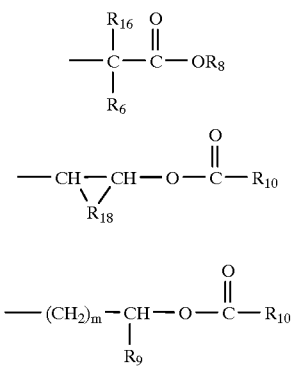

in which m is a number from the range 1 to 12;

$R_6$ is $C_1$–$C_{16}$alkyl, —COOR$_8$ or phenyl;

$R_8$ is H, $C_1$–$C_{18}$alkyl, $C_3$–$C_{18}$alkenyl, $C_5$–$C_{12}$cycloalkyl, $C_1$–$C_4$alkylcyclohexyl, phenyl, $C_7$–$C_{14}$alkylphenyl, $C_6$–$C_{15}$bicycloalkyl, $C_6$–$C_{15}$-bicycloalkenyl, $C_6$–$C_{15}$tricycloalkyl, $C_6$–$C_{15}$bicycloalkyl-alkyl or $C_7$–$C_{11}$phenylalkyl, and, if Z is a group of the formula II, additionally comprises $C_2$–$C_{50}$alkyl interrupted by O;

$R_9$ is $C_2$–$C_{14}$alkyl, phenyl, or $C_2$–$C_{50}$alkyl interrupted by O; or is $C_1$–$C_{14}$alkyl which is substituted by phenyl, phenoxy, $C_1$–$C_4$alkylcyclohexyl, $C_1$–$C_4$alkylcyclohexyloxy, $C_5$–$C_{12}$cycloalkyl or $C_5$–$C_{12}$cycloalkoxy;

$R_{10}$ is H, $C_1$–$C_{17}$alkyl, $C_1$–$C_{12}$alkoxy, phenoxy, phenyl, $C_7$–$C_{11}$phenylalkyl, $C_7$–$C_{14}$alkylphenoxy, $C_7$–$C_{11}$phenylalkoxy, $C_6$–$C_{12}$cycloalkyl, $C_1$–$C_4$alkyl-cyclohexyloxy, $C_6$–$C_{12}$cycloalkoxy, $C_7$–$C_{11}$cyclohexylalkyl, $C_7$–$C_{11}$cyclohexylalkoxy, $C_6$–$C_{15}$bicycloalkyl, $C_6$–$C_{15}$bicycloalkenyl, $C_6$–$C_{15}$tricycloalkyl, $C_6$–$C_{15}$bicycloalkoxy, $C_6$–$C_{15}$bicycloalkenoxy, $C_6$–$C_{15}$tricycloalkoxy or phenyl-NH—;

$R_{16}$ is hydrogen or is as defined for $R_6$; or $R_6$ and $R_{16}$ together are $C_4$–$C_{11}$alkylene; and $R_{18}$ is $C_3$–$C_{10}$alkylene, with the exception of those compounds in which Z is a group of the formula III and $R_1$ and $R_5$ are both alkyl, and of those in which $R_3$ or $R_{13}$ is phenyl and $R_7$ or $R_{17}$ is a radical of the formula VI or $R_{16}$ is hydrogen.

2. A composition according to claim 1, in which component A is a thermoplastic polymer or a binder for coatings.

3. A composition according to claim 1 containing from 0.01 to 15 parts by weight of component B per 100 parts by weight of component A.

4. A composition according to claim 1 comprising in addition to the stabilizer of the formula I other stabilizers or other additives.

5. A composition according to claim 1, in which component A is a binder for coatings.

6. A composition according to claim 5 comprising, in addition to components A and B, as component C a light stabilizer of the sterically hindered amine, 2-(2-hydroxyphenyl)-1,3,5-triazine and/or 2-hydroxyphenyl-2 H-benzotriazole type.

7. A composition according to claim 1, in which in formula I of component B $R_1$, $R_5$, $R_{11}$ and $R_{15}$, independently of one another, are H, $C_1$–$C_4$alkyl, $C_3$alkenyl, $C_1$–$C_4$alkoxy, $C_3$–$C_6$alkenoxy, —F or —Cl;

$R_2$, $R_3$, $R_4$, $R_{12}$, $R_{13}$ and $R_{14}$, independently of one another, are H, $C_1$–$C_4$alkyl, $C_3$–$C_6$alkenyl, $C_1$–$C_4$alkoxy, $C_3$–$C_6$alkenoxy, phenyl, —F, —Cl, or —CN; $R_6$ is $C_1$–$C_{16}$alkyl or phenyl;

$R_8$ is H, $C_1$–$C_{18}$alkyl, $C_3$–$C_8$alkenyl, cyclohexyl, $C_1$–$C_4$alkylcyclohexyl, phenyl, norborn-2-yl, norborn-5-en-2-yl, norborn-2-methyl, norborn-5-ene-2-methyl or $C_7$–$C_{11}$phenylalkyl and, if Z is a group of the formula II, additionally comprises $C_2$–$C_{18}$alkyl interrupted by O;

$R_9$ is $C_2$–$C_{14}$alkyl or $C_3$–$C_{14}$alkyl interrupted by O, or phenyl;

$R_{10}$ is H, $C_1$–$C_{17}$alkyl, $C_1$–$C_{12}$alkoxy, phenoxy, phenyl, $C_7$–$C_{11}$phenylalkyl, cyclohexyl, $C_7$–$C_{11}$cyclohexylalkyl, norbornyl, norbornenyl, 1-adamantyl or phenyl-NH—;

$R_{16}$ is hydrogen or is as defined for $R_6$; and $R_{18}$ is $C_3$–$C_{10}$alkylene.

8. A composition according to claim 1, in which in formula I of component B $R_6$ is $C_1$–$C_{16}$alkyl;

$R_8$ is $C_1$–$C_{18}$alkyl, $C_3$alkenyl, cyclohexyl, methylcyclohexyl, phenyl or benzyl and, if Z is a group of the formula II, additionally comprises $C_3$–$C_{13}$alkyl interrupted by O;

$R_9$ is $C_2$–$C_{14}$alkyl or $C_3$–$C_{14}$alkyl interrupted by O, or phenyl;

$R_{10}$ is $C_1$–$C_{17}$alkyl, $C_1$–$C_{12}$alkoxy, phenyl, $C_7$–$C_{11}$phenylalkyl, cyclohexyl or phenyl-NH—;

$R_{16}$ is hydrogen or is as defined for $R_6$; and $R_{18}$ is $C_3$–$C_{10}$alkylene.

9. A composition according to claim 1, in which in formula I of component B $R_1$, $R_5$, $R_{11}$ and $R_{15}$, independently of one another, are H or $C_1$–$C_4$alkyl; $R_2$, $R_3$, $R_4$, $R_{12}$, $R_{13}$ and $R_{14}$, independently of one another, are H, $C_1$–$C_4$alkyl, methoxy, phenyl, —F, —Cl, benzyl or —CN;

m is a number from the range 1 to 8;

$R_6$ is $C_1$–$C_{16}$alkyl;

$R_8$ is $C_1$–$C_{10}$alkyl, $C_3$alkenyl, cyclohexyl or phenyl and, if Z is a group of the formula II, additionally comprises $C_3$–$C_{13}$alkyl interrupted by O;

$R_9$ is $C_2$–$C_8$alkyl or $C_3$–$C_{12}$alkyl interrupted by O;

$R_{10}$ is $C_1$–$C_{17}$alkyl, $C_1$–$C_{12}$alkoxy or cyclohexyl;

$R_{16}$ is hydrogen or is as defined for $R_6$; and $R_{18}$ is $C_3$–$C_6$alkylene.

10. A composition according to claim 1, in which in formula I of component B $R_1$, $R_2$, $R_3$, $R_4$, $R_5$, $R_{11}$, $R_{12}$, $R_{13}$, $R_{14}$ and $R_{15}$, independently of one another, are H or methyl;

$R_7$ and $R_{17}$, independently of one another, are a radical of one of the formulae IV, V and VI, in which m is 1;

$R_6$ is $C_1$–$C_8$alkyl;

$R_8$ is $C_1$–$C_{17}$alkyl, and, if Z is a group of the formula II, additionally comprises $C_3$–$C_8$alkyl interrupted by O;

$R_9$ is —CH$_2$O—R$_9$;

$R_{10}$ is $C_1$–$C_{17}$alkyl or $C_2$–$C_8$alkoxy;

$R_{16}$ is hydrogen or $C_1$–$C_8$alkyl;

$R_{18}$ is $C_3$–$C_6$alkylene and $R_{19}$ is $C_2$–$C_{13}$alkyl.

11. A process for stabilizing synthetic organic polymers or prepolymers against damage by light, oxygen and/or heat, which comprises adding thereto a compound of the formula I according to claim 1 as stabilizer.

12. A compound of the formula I'

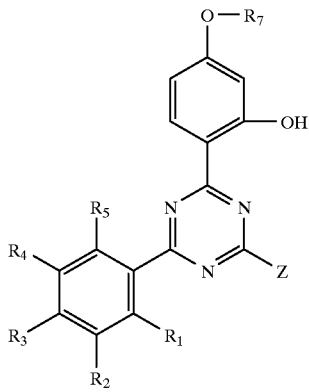

(I')

in which Z is a group of the formula II

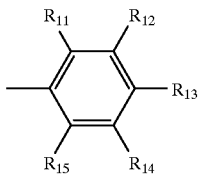

(II')

or a group of the formula III'

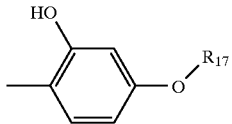

(III')

$R_1$, $R_5$, $R_{11}$ and $R_{15}$, independently of one another, are H, $C_1$–$C_{12}$alkyl, $C_3$–$C_6$alkenyl, $C_1$–$C_{12}$alkoxy, $C_3$–$C_6$alkenoxy, halogen or —CN;

$R_2$, $R_3$, $R_4$, $R_{12}$, $R_{13}$ and $R_{14}$, independently of one another, are H, $C_1$–$C_{12}$alkyl, $C_2$–$C_6$alkenyl, $C_1$–$C_{12}$alkoxy, $C_3$–$C_6$alkenoxy, phenyl, halogen, trifluoromethyl, $C_7$–$C_{11}$phenylalkyl, phenyloxy or —CN;

$R_7$ and $R_{17}$, independently of one another, are a radical of one of the formulae IV', V' and VI'

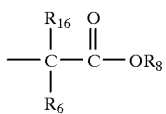

(IV')

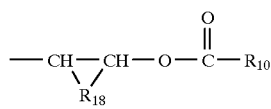

(V')

-continued (VI')

—(CH$_2$)$_m$—CH—O—C—R$_{10}$
            |           ‖
            R$_9$         O in which m is a number from the range 1 to 12;

$R_6$ is $C_1$–$C_{16}$alkyl, —COOR$_8$ or phenyl;

$R_8$ is H, $C_1$–$C_{18}$alkyl, $C_3$–$C_{18}$alkenyl, $C_5$–$C_{12}$cycloalkyl, $C_1$–$C_4$alkylcyclohexyl, phenyl, $C_7$–$C_{14}$alkylphenyl, $C_6$–$C_{15}$bicycloalkyl, $C_6$–$C_{15}$-bicycloalkenyl, $C_6$–$C_{15}$tricycloalkyl, $C_6$–$C_{15}$bicycloalkyl-alkyl or $C_7$–$C_{11}$ phenylalkyl, and, if Z is a group of the formula II, additionally comprises $C_2$–$C_{18}$alkyl interrupted by O;

$R_9$ is $C_2$–$C_{14}$alkyl or phenyl; or is $C_1$–$C_{14}$alkyl which is substituted by phenyl, phenoxy, $C_1$–$C_4$alkylcyclohexyl, $C_1$–$C_4$alkylcyclohexyloxy, $C_5$–$C_{12}$cycloalkyl or $C_5$–$C_{12}$cycloalkoxy;

$R_{10}$ is H, $C_1$–$C_{17}$alkyl, $C_1$–$C_{12}$alkoxy, phenoxy, phenyl, $C_7$–$C_{11}$phenylalkyl, $C_7$–$C_{14}$alkylphenoxy, $C_7$–$C_{11}$phenylalkoxy, $C_6$–$C_{12}$cycloalkyl, $C_1$–$C_4$alkylcyclohexyloxy, $C_6$–$C_{12}$cycloalkoxy, $C_7$–$C_{11}$cyclohexylalkyl, $C_7$–$C_{11}$cyclohexylalkoxy, $C_6$–$C_{15}$bicycloalkyl, $C_6$–$C_{15}$bicycloalkenyl, $C_6$–$C_{15}$tricycloalkyl, $C_6$–$C_{15}$bicycloalkoxy, $C_6$–$C_{15}$bicycloalkenoxy, $C_6$–$C_{15}$tricycloalkoxy or phenyl-NH—;

$R_{16}$ is as defined for $R_6$ and, if Z is a croup of the formula II, additionally comprises hydrogen; and $R_{18}$ is $C_3$–$C_{10}$alkylene, with the exception of those compounds in which Z is a group of the formula III and $R_1$ and $R_5$ are both alkyl, and of those in which $R_3$ or $R_{13}$ is phenyl and $R_7$ or $R_{17}$ is a radical of the formula VI' or $R_{16}$ is hydrogen.

13. A compound of the formula I' according to claim 12, in which $R_1$, $R_5$, $R_{11}$, and $R_{15}$, independently of one another, are H, $C_1$–$C_4$alkyl, $C_3$alkenyl, $C_1$–$C_4$alkoxy, $C_3$–$C_6$alkenoxy, —F or —Cl; $R_2$, $R_3$, $R_4$, $R_{12}$, $R_{13}$ and $R_{14}$, independently of one another, are H, $C_1$–$C_4$alkyl, $C_3$–$C_6$alkenyl, $C_1$–$C_4$alkoxy, $C_3$–$C_6$alkenoxy, phenyl, —F, —Cl, or —CN;

$R_6$ is $C_1$–$C_{16}$alkyl or phenyl;

$R_8$ is H, $C_1$–$C_{18}$alkyl, $C_3$–$C_8$alkenyl, cyclohexyl, $C_1$–$C_4$alkylcyclohexyl, phenyl, or $C_7$–$C_{11}$phenylalkyl and, if Z is a group of the formula II, additionally comprises $C_2$–$C_{18}$alkyl interrupted by O;

$R_9$ is $C_2$–$C_{14}$alkyl;

$R_{10}$ is H, $C_1$–$C_{17}$alkyl, $C_1$–$C_{12}$alkoxy, phenoxy, phenyl, $C_7$–$C_{11}$phenylalkyl, cyclohexyl, $C_7$–$C_{11}$cyclohexylalkyl, or phenyl-NH—;

$R_{16}$ is as defined for $R_6$; and, if Z is a group of the formula II, additionally comprises hydrogen; and $R_{18}$ is $C_3$–$C_{10}$alkylene.

14. A compound of the formula I' according to claim 12, in which $R_6$ is $C_1$–$C_{16}$alkyl;

$R_8$ is $C_1$–$C_{18}$alkyl, $C_3$alkenyl, cyclohexyl, phenyl or benzyl and, if Z is a group of the formula II, additionally comprises $C_3$–$C_{13}$alkyl interrupted by O;

$R_{10}$ is $C_1$–$C_{17}$alkyl, $C_1$–$C_{12}$alkoxy, phenyl, $C_7$–$C_{11}$ phenylalkyl, cyclohexyl or phenyl-NH—; and $R_{18}$ is $C_3$–$C_6$alkylene.

15. A compound of the formula I' according to claim 12, in which $R_1$, $R_5$, $R_{11}$ and $R_{15}$, independently of one another, are H or $C_1$–$C_4$alkyl;

$R_2$, $R_3$, $R_4$, $R_{12}$, $R_{13}$ and $R_{14}$, independently of one another, are H, $C_1$–$C_4$alkyl, methoxy, phenyl, —F, —Cl, benzyl or —CN;

m is a number from the range 1 to 8;

$R_6$ is $C_1$–$C_{16}$alkyl;

$R_8$ is $C_1$–$C_{15}$alkyl, $C_3$alkenyl, cyclohexyl or phenyl and, if Z is a group of the formula II, additionally comprises $C_3$–$C_{13}$alkyl interrupted by O;

$R_9$ is $C_2$–$C_8$alkyl;

$R_{10}$ is $C_1$–$C_{17}$alkyl, $C_1$–$C_{12}$alkoxy or cyclohexyl and $R_{18}$ is $C_3$–$C_6$alkylene.

16. A composition comprising

A) an organic material which is sensitive to damage by light, oxygen and/or heat, and B) as stabilizer, a compound of the formula I' according to claim 12.

17. One of the compounds 2,4-diphenyl-6-(2'-hydroxy-4'-(2"-hydroxycyclohexyloxy)phenyl)-1,3,5-triazine, 2,4-bis(2',4'-dimethylphenyl)-6-(2'-hydroxy-4'-(2"-hydroxycyclohexyloxy)phenyl)-1,3,5-triazine, 2-phenyl-4,6-bis(2'-hydroxy-4'-(2"-hydroxycyclohexyloxy)phenyl)-1,3,5-triazine.

\* \* \* \* \*